(12) United States Patent
Imamura et al.

(10) Patent No.: US 12,133,751 B2
(45) Date of Patent: Nov. 5, 2024

(54) RADIOGRAPHY APPARATUS AND METHOD FOR CONTROLLING RADIOGRAPHY APPARATUS

(71) Applicant: FUJIFILM CORPORATION, Tokyo (JP)

(72) Inventors: Ryo Imamura, Kanagawa (JP); Koichi Eguchi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 233 days.

(21) Appl. No.: 17/674,855

(22) Filed: Feb. 18, 2022

(65) Prior Publication Data

US 2022/0167934 A1 Jun. 2, 2022

Related U.S. Application Data

(63) Continuation of application No. PCT/JP2020/036593, filed on Sep. 28, 2020.

(30) Foreign Application Priority Data

Sep. 30, 2019 (JP) .................................. 2019-180016
Oct. 31, 2019 (JP) .................................. 2019-199332

(51) Int. Cl.
*A61B 6/00* (2024.01)

(52) U.S. Cl.
CPC .......... *A61B 6/4452* (2013.01); *A61B 6/4441* (2013.01); *A61B 6/5264* (2013.01)

(58) Field of Classification Search
CPC ... A61B 6/4405; A61B 6/4441; A61B 6/4452; A61B 6/5264; A61B 6/54
See application file for complete search history.

(56) References Cited

U.S. PATENT DOCUMENTS

2008/0011958 A1* 1/2008 Endo ..................... H04N 5/32
                                                    250/370.08
2008/0095324 A1* 4/2008 Watanabe ............ A61B 6/4441
                                                    378/198
(Continued)

FOREIGN PATENT DOCUMENTS

DE    102004022804 B3 *  9/2005  .......... A61B 6/4405
EP         0231969 A1     8/1987
(Continued)

OTHER PUBLICATIONS

Translated DE-102004022804 (Year: 2005).*
(Continued)

*Primary Examiner* — Dani Fox
*Assistant Examiner* — Soorena Kefayati
(74) *Attorney, Agent, or Firm* — SOLARIS Intellectual Property Group, PLLC

(57) ABSTRACT

A radiography apparatus includes: an irradiation unit that emits radiation; an arm that holds the irradiation unit and an image receiving unit in a facing posture such that the image receiving unit is attachable and detachable; a connection portion or a main body portion that rotatably supports the arm; a first locking mechanism and a second locking mechanism that lock a rotation of the arm with respect to the connection portion or the main body portion; a photo sensor that detects whether or not the image receiving unit is detached from the arm; and a control unit that performs control not to release the lock even in a case in which an unlock operation for releasing the lock of the rotation by the first locking mechanism and the second locking mechanism is performed in a state in which the image receiving unit is detached from the arm.

7 Claims, 25 Drawing Sheets

(56) References Cited

U.S. PATENT DOCUMENTS

| | | | | |
|---|---|---|---|---|
| 2009/0040333 A1* | 2/2009 | Koyanagi | ............... | A61B 6/447 |
| | | | | 348/E9.051 |
| 2011/0142199 A1* | 6/2011 | Kantor | ................ | A61B 6/4441 |
| | | | | 378/39 |
| 2012/0106701 A1* | 5/2012 | Meek | ....................... | H05G 1/02 |
| | | | | 474/84 |
| 2014/0029719 A1* | 1/2014 | Lee | ..................... | A61B 6/4429 |
| | | | | 378/38 |
| 2014/0037058 A1* | 2/2014 | Allen | .................. | A61B 6/4441 |
| | | | | 378/62 |
| 2015/0223767 A1* | 8/2015 | Sehnert | .................. | A61B 6/547 |
| | | | | 378/42 |
| 2016/0291172 A1* | 10/2016 | Ono | ....................... | A61B 6/486 |
| 2018/0298970 A1* | 10/2018 | Daugirdas | ............ | A61B 6/4476 |

FOREIGN PATENT DOCUMENTS

| | | |
|---|---|---|
| EP | 1847220 A2 | 10/2007 |
| JP | S62-183746 A | 8/1987 |
| JP | H06-70918 A | 3/1994 |
| JP | H10-225450 A | 8/1998 |
| JP | 2002-102214 A | 4/2002 |
| JP | 2004-073356 A | 3/2004 |
| JP | 2006-280517 A | 10/2006 |
| JP | 2008-245726 A | 10/2008 |
| JP | 2009-39332 A | 2/2009 |
| JP | 2010-012180 A | 1/2010 |
| JP | 2012-525899 A | 10/2012 |
| JP | 2013-078648 A | 5/2013 |
| JP | 2013-128593 A | 7/2013 |
| JP | 2018-175872 A | 11/2018 |

OTHER PUBLICATIONS

Extended European Search Report dated Oct. 21, 2022, issued in corresponding EP Patent Application No. 20872487.2.

English language translation of the following: Office action dated May 17, 2022 from the JPO in a Japanese patent application No. 2019-180016 corresponding to the instant patent application. This office action translation is submitted now in order to supplement the understanding of the cited references which are being disclosed in the instant Information Disclosure Statement.

International Search Report issued in International Application No. PCT/JP2020/036593 on Nov. 24, 2020.

Written Opinion of the ISA issued in International Application No. PCT/JP2020/036593 on Nov. 24, 2020.

English language translation of the following: Office action dated Feb. 15, 2022 from the JPO in a Japanese patent application No. 2019-180016 corresponding to the instant patent application.

English language translation of the following: Office action dated Feb. 15, 2022 from the JPO in a Japanese patent application No. 2019-199332 corresponding to the instant patent application.

\* cited by examiner

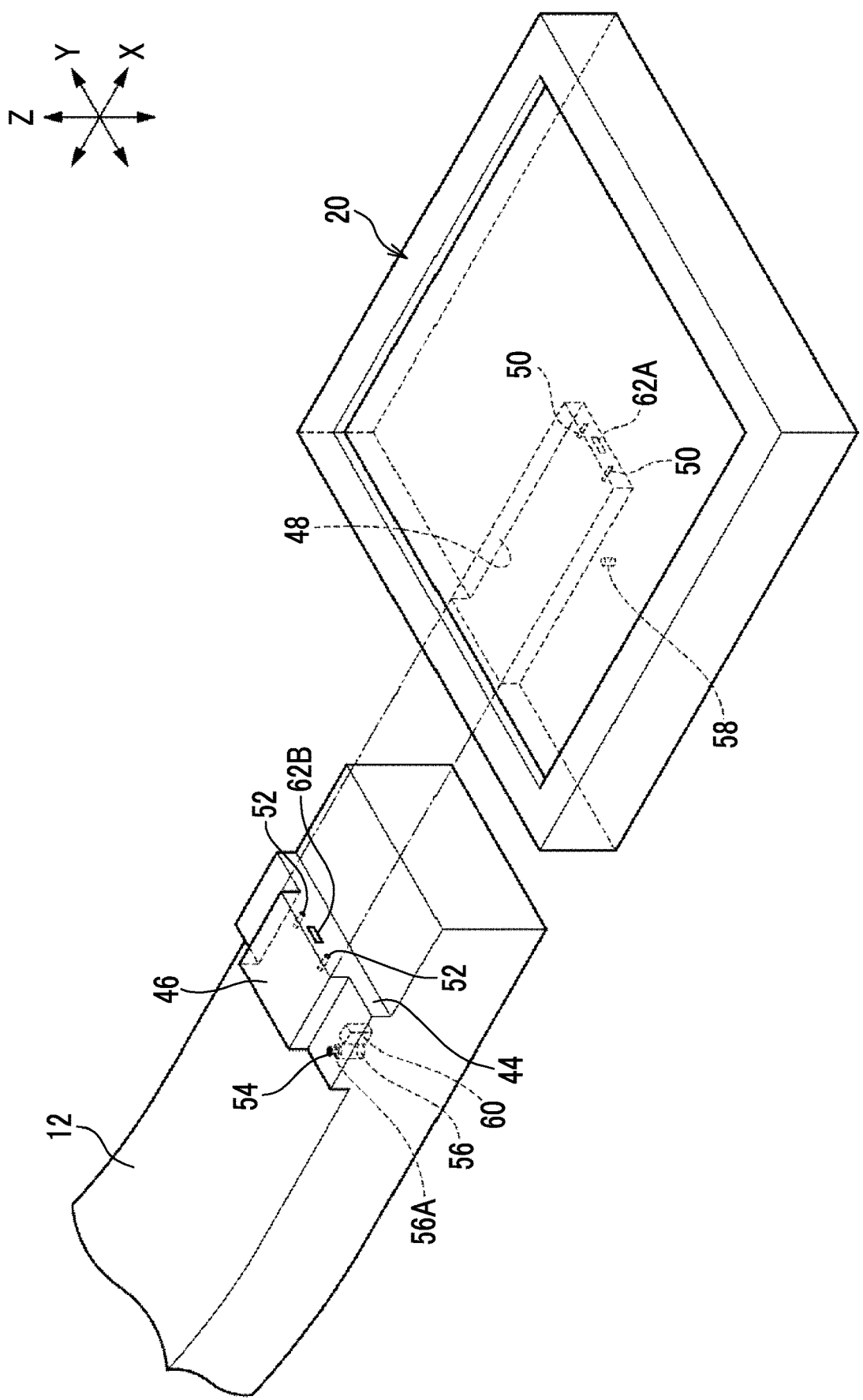

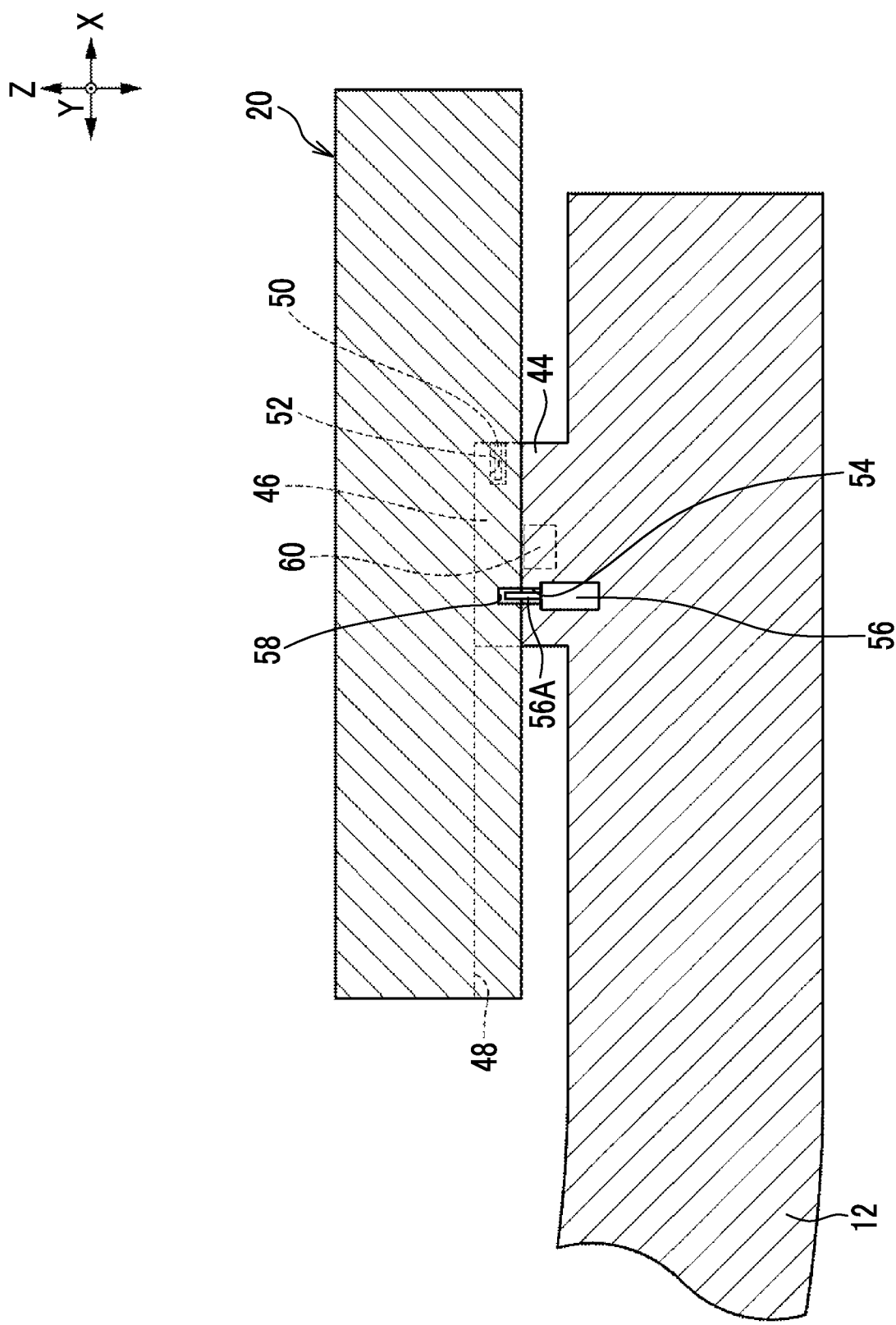

RADIOGRAPHY APPARATUS AND METHOD FOR CONTROLLING RADIOGRAPHY APPARATUS

CROSS-REFERENCE TO RELATED APPLICATIONS

This application is a continuation application of International Application No. PCT/JP2020/036593, filed Sep. 28, 2020, the disclosure of which is incorporated herein by reference in its entirety. Further, this application claims priority from Japanese Patent Application No. 2019-199332, filed on Oct. 31, 2019, and Japanese Patent Application No. 2019-180016, filed on Sep. 30, 2019, the disclosures of which are incorporated herein by reference in their entireties.

BACKGROUND

1. Technical Field

The present disclosure relates to a radiography apparatus and a method for controlling a radiography apparatus.

2. Description of the Related Art

A radiography apparatus is known which comprises an arm having one end at which an irradiation unit emitting radiation is provided. Among the radiography apparatuses, a radiography apparatus is known that has an arm which has two ends and in which an irradiation unit is provided at one end and an image receiving unit is detachably attached to the other end (see JP2009-39332A).

The radiography apparatus disclosed in JP2009-39332A comprises the arm (referred to as a C-arm or the like) that has a C-shape in a side view. The arm is rotatable with respect to a main body portion of the radiography apparatus which supports the arm. The arm is rotated such that the irradiation unit (radiation generation device) and the image receiving unit (imaging unit) provided at both ends of the arm are positioned in an any posture around the subject while maintaining a relative position.

Further, in the radiography apparatus disclosed in JP2009-39332A, the amount of liquid in a weight adjustment tank is adjusted to adjust a weight balance of the arm in order to hold the irradiation unit (radiation generation device) and the image receiving unit (imaging unit) in an any posture. In particular, in a case in which the image receiving unit (imaging unit) is attached to or detached from the arm, the weight balance of the arm changes rapidly, which may cause the inadvertent rotation of the arm.

Therefore, the radiography apparatus disclosed in JP2009-39332A starts to adjust the weight balance in a case in which the attachment or detachment of the image receiving unit (imaging unit) to or from the arm is detected. Then, an operation of rotating the arm is disabled until the adjustment of the weight balance ends. The operation of rotating the arm is permitted after the adjustment of the weight balance ends.

SUMMARY

However, a weight balance adjustment mechanism disclosed in JP2009-39332A requires, for example, a weight adjustment tank, a liquid, and a pump for transferring the liquid and has a complicated configuration.

The technology according to the present disclosure provides a radiography apparatus and a method for controlling a radiography apparatus which can suppress the inadvertent rotation of an arm in a case in which an image receiving unit is detached, without using a complicated mechanism.

According to a first aspect of the present disclosure, there is provided a radiography apparatus comprising: an irradiation unit that emits radiation; an arm that holds the irradiation unit and an image receiving unit that receives the radiation, which has been emitted from the irradiation unit and transmitted through a subject, in a facing posture such that the image receiving unit is attachable and detachable; a support portion that rotatably supports the arm; a locking mechanism that locks a rotation of the arm with respect to the support portion; a first attachment and detachment detection unit that detects whether or not the image receiving unit is detached from the arm; and a control unit that performs control to prohibit a release of the lock even in a case in which an unlock operation for releasing the lock of the rotation by the locking mechanism is performed in a state in which the first attachment and detachment detection unit detects that the image receiving unit is detached from the arm.

According to the above configuration, the control unit of the radiography apparatus performs control to prohibit the release of the lock even in a case in which the unlock operation for releasing the lock of the rotation by the locking mechanism in a state in which the image receiving unit is detached from the arm. Therefore, it is possible to suppress the inadvertent rotation of the arm in a case in which the image receiving unit is detached, without using a complicated mechanism.

According to a second aspect of the present disclosure, in the radiography apparatus according to the first aspect, the image receiving unit may include a detector that receives the radiation, which has been emitted from the irradiation unit and transmitted through the subject, to detect a radiographic image of the subject, and the detector may be provided in a housing to be undetachable.

According to a third aspect of the present disclosure, in the radiography apparatus according to the first aspect, the image receiving unit may include a detector that receives the radiation, which has been emitted from the irradiation unit and transmitted through the subject, to detect a radiographic image of the subject and an accommodation portion in which the detector is attachably and detachably accommodated, and the accommodation portion may be held to be attachable to and detachable from the arm.

According to a fourth aspect of the present disclosure, the radiography apparatus according to the third aspect may further comprise: a friction mechanism that is switchable between a first state in which a frictional force is applied to the arm in a direction opposite to a direction in which the arm is rotated and a second state in which the frictional force applied to the arm is less than the frictional force in the first state; and a second attachment and detachment detection unit that detects whether or not the detector is detached from the accommodation portion. The first attachment and detachment detection unit may detect whether or not the accommodation portion is detached from the arm. In a case in which the unlock operation is performed in a state in which the first attachment and detachment detection unit detects that the accommodation portion is attached to the arm and the second attachment and detachment detection unit detects that the detector is detached from the accommodation portion, the control unit may perform control to permit the release of the lock by the locking mechanism and to switch the friction mechanism to the first state.

In a state in which the accommodation portion is attached to the arm and the detector is detached from the accommodation portion, a change in the weight balance of the arm is smaller than that in a state in which both the accommodation portion and the detector are detached from the arm.

Here, according to the above configuration, in a state in which the accommodation portion is attached to the arm and the detector is detached from the accommodation portion, the release of the lock of the rotation of the arm is permitted, and the friction mechanism is switched to the first state in which the frictional force is applied in the direction opposite to the direction in which the arm is rotated. Therefore, it is possible to suppress the inadvertent rotation of the arm with the frictional force.

According to a fifth aspect of the present disclosure, in the radiography apparatus according to the fourth aspect, in a case in which the unlock operation is performed in a state in which the first attachment and detachment detection unit detects that the accommodation portion is attached to the arm and the second attachment and detachment detection unit detects that the detector is attached to the accommodation portion, the control unit may perform control to permit the release of the lock by the locking mechanism and to switch the friction mechanism to the second state.

According to the above configuration, in a state in which the accommodation portion is attached to the arm and the detector is attached to the accommodation portion, the release of the lock of the rotation of the arm is permitted, and the friction mechanism is switched to the second state in which the frictional force applied to the arm is less than the frictional force in the first state. Therefore, it is possible to easily rotate the arm about the support shaft.

According to a sixth aspect of the present disclosure, the radiography apparatus according to any one of the third to fifth aspects may further comprise: a rotation angle restriction mechanism that is switchable between a restricted state in which a range of a rotation angle of the arm is restricted to a second range narrower than a first range and a derestricted state in which a restriction of the rotation angle is released; and a second attachment and detachment detection unit that detects whether or not the detector is detached from the accommodation portion. The first attachment and detachment detection unit may detect whether or not the accommodation portion is detached from the arm. In a case in which the unlock operation is performed in a state in which the first attachment and detachment detection unit detects that the accommodation portion is attached to the arm and the second attachment and detachment detection unit detects that the detector is detached from the accommodation portion, the control unit may perform control to permit the release of the lock by the locking mechanism and to switch the rotation angle restriction mechanism to the restricted state.

In a state in which the accommodation portion is attached to the arm and the detector is detached from the accommodation portion, a change in the weight balance of the arm is smaller than that in a state in which both the accommodation portion and the detector are detached from the arm.

Here, according to the above configuration, in a state in which the accommodation portion is attached to the arm and the detector is detached from the accommodation portion, to permit the release of the lock by the locking mechanism and to switch the rotation angle restriction mechanism to the derestricted state in which the rotation angle of the arm is restricted to the second range narrower than the first range. Therefore, it is possible to restrict the inadvertent rotation of the arm.

According to a seventh aspect of the present disclosure, in the radiography apparatus according to the sixth aspect, in a case in which the unlock operation is performed in a state in which the first attachment and detachment detection unit detects that the accommodation portion is attached to the arm and the second attachment and detachment detection unit detects that the detector is attached to the accommodation portion, the control unit may perform control to permit the release of the lock by the locking mechanism and to switch the rotation angle restriction mechanism to the derestricted state.

According to the above configuration, in a state in which the accommodation portion is attached to the arm and the detector is attached to the accommodation portion, the release of the lock of the rotation of the arm is permitted, and the rotation angle restriction mechanism is switched to the derestricted state in which the restriction of the rotation angle of the arm is released. Therefore, the rotation angle of the arm can be set to the first range.

According to an eighth aspect of the present disclosure, in the radiography apparatus according to any one of the first to seventh aspects, the arm may have an arc shape in a side view, the support portion may include a track portion that supports the arm to be movable along the arc shape, and the arm may be moved with respect to the track portion to be orbitally rotatable about a center of the arc shape as a rotation center.

According to the above configuration, the arm can be orbitally rotated about the center of the arc shape as a rotation center with respect to the track portion. Therefore, the irradiation unit and the image receiving unit can be rotated about the body axis of the subject.

According to a ninth aspect of the present disclosure, in the radiography apparatus according to any one of the first to eighth aspects, the support portion may include a bearing portion that supports one end of a support shaft having the other end fixed to the arm, and the arm may be rotated about the support shaft with respect to the bearing portion to reverse positions of the irradiation unit and the image receiving unit with respect to the subject.

According to the above configuration, the arm can be rotated about the support shaft with respect to the bearing portion. Therefore, it is possible to reverse the positions of the irradiation unit and the image receiving unit with respect to the subject.

According to a tenth aspect of the present disclosure, in the radiography apparatus according to any one of the first to seventh aspects, while the irradiation unit continuously emits the radiation in a state in which the first attachment and detachment detection unit detects that the image receiving unit is attached to the arm, the control unit may perform control to prohibit the release of the lock even in a case in which the unlock operation for releasing the lock of the rotation by the locking mechanism is performed.

According to the above configuration, in a case in which the image receiving unit is attached to the arm, the release of the rotation of the lock of the arm is prohibited during the capture of a moving image when the irradiation unit continuously emits the radiation even though the unlock operation is performed. Therefore, it is possible to suppress the unnecessary irradiation of parts other than a target imaging part with radiation because of the inadvertent rotation of the arm.

According to an eleventh aspect of the present disclosure, there is provided a method for controlling a radiography apparatus including an arm that holds an irradiation unit that emits radiation and an image receiving unit that receives the radiation, which has been emitted from the irradiation unit and transmitted through a subject, in a facing posture such that the image receiving unit is attachable and detachable, a support portion that rotatably supports the arm, and a locking mechanism that locks a rotation of the arm with respect to the support portion. The method comprises: detecting whether or not the image receiving unit is detached from the arm; and performing control to prohibit a release of the lock even in a case in which an unlock operation for releasing the lock of the rotation by the locking mechanism is performed in a state in which it is detected that the image receiving unit is detached from the arm.

According to the above configuration, even in a case in which the unlock operation for releasing the lock of the rotation by the locking mechanism is performed in a state in which the image receiving unit is detached from the arm, the control to prohibit the release of the lock is performed. Therefore, it is possible to suppress the inadvertent rotation of the arm in a case in which the image receiving unit is detached, without using a complicated mechanism.

According to the technology of the present disclosure, it is possible to suppress the inadvertent rotation of the arm in a case in which the image receiving unit is detached, without using a complicated mechanism.

BRIEF DESCRIPTION OF THE DRAWINGS

Exemplary embodiments according to the technique of the present disclosure will be described in detail based on the following figures, wherein:

FIG. 4A is a partial perspective view illustrating an image receiving unit of the radiography apparatus according to the first embodiment, FIG. 4B is a cross-sectional view illustrating the image receiving unit illustrated in FIG. 4A.

DETAILED DESCRIPTION

Figure 1:
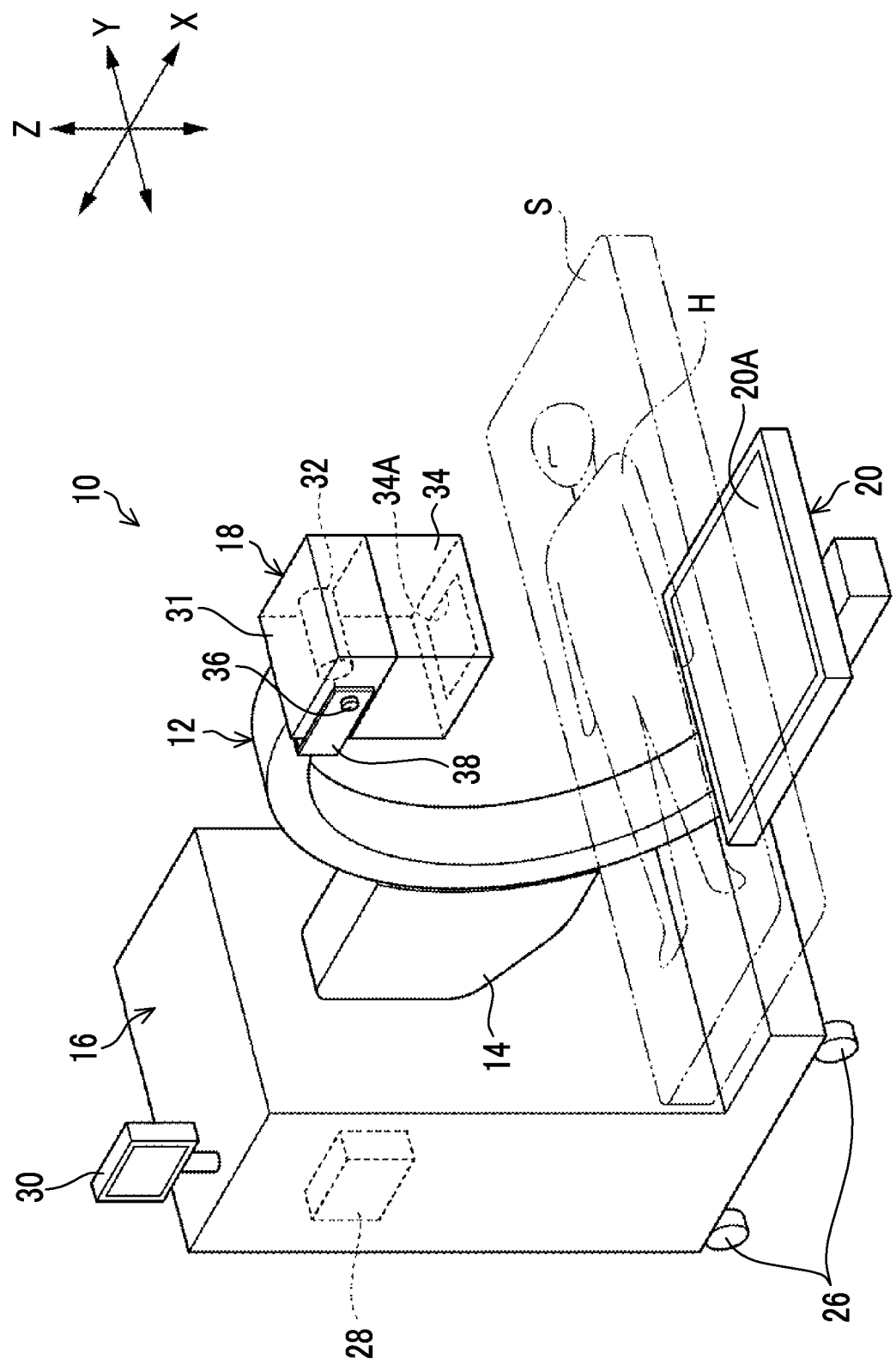
FIG. 1 is an overall perspective view illustrating a radiography apparatus according to a first embodiment.

Hereinafter, radiography apparatuses according to first to third embodiments of the present disclosure will be sequentially described with reference to the drawings. In addition, in the drawings, an arrow X indicates a front-rear direction of the radiography apparatus, an arrow Y indicates a width direction of the radiography apparatus, and an arrow Z indicates a vertical direction.

First Embodiment

First, a radiography apparatus according to the first embodiment of the present disclosure will be described with reference to FIGS. 1 to 10.

(Overall Configuration of Radiography Apparatus)

A radiography apparatus 10 according to this embodiment illustrated in FIG. 1 is an apparatus that captures a radiographic image of a subject H. The radiography apparatus 10 can capture, for example, moving images and still images of the subject H. The capture of the moving image is performed, for example, in a case in which a treatment target part of the subject H is displayed as a moving image during surgery (also referred to as fluoroscopy). In the capture of the moving image, for example, the moving image of the subject H is displayed on a monitor (not illustrated) that is provided separately from the radiography apparatus 10. Of course, data of the captured moving image may be stored in a memory of the radiography apparatus 10. In addition, in the case of the capture of the still image, the captured still image may be displayed on the monitor or may be stored in the memory of the radiography apparatus 10.

As illustrated in FIG. 1, the radiography apparatus 10 includes an arm 12 (referred to as a C-arm or the like) which has a C-shape (an arc shape) in a side view and a connection portion 14 and a main body portion 16 which serve as a support portion rotatably supporting the arm 12. In addition, hereinafter, it is assumed that the side of the radiography apparatus 10 on which the arm 12 is provided is the front side of the radiography apparatus 10 and the side on which the main body portion 16 is provided is the rear side of the radiography apparatus 10.

(Configuration of Arm)

The arm 12 has two ends. An irradiation unit 18 is provided at one end of the arm 12, and an image receiving unit 20 is provided at the other end. The arm 12 can hold the irradiation unit 18 and the image receiving unit 20 in a posture in which they face each other. A space, into which the subject H and a bed S on which the subject H lies supine can be inserted, is ensured between the irradiation unit 18 and the image receiving unit 20. Further, in the following description, in some cases, in a side view of the arm 12 (as viewed from the Y direction in FIG. 1), a direction in which the irradiation unit 18 and the image receiving unit 20 are provided on the basis of the arm 12 is referred to as the front side of the arm 12 and the side of the arm 12 is referred to as the rear side of the arm 12.

Figure 2A:
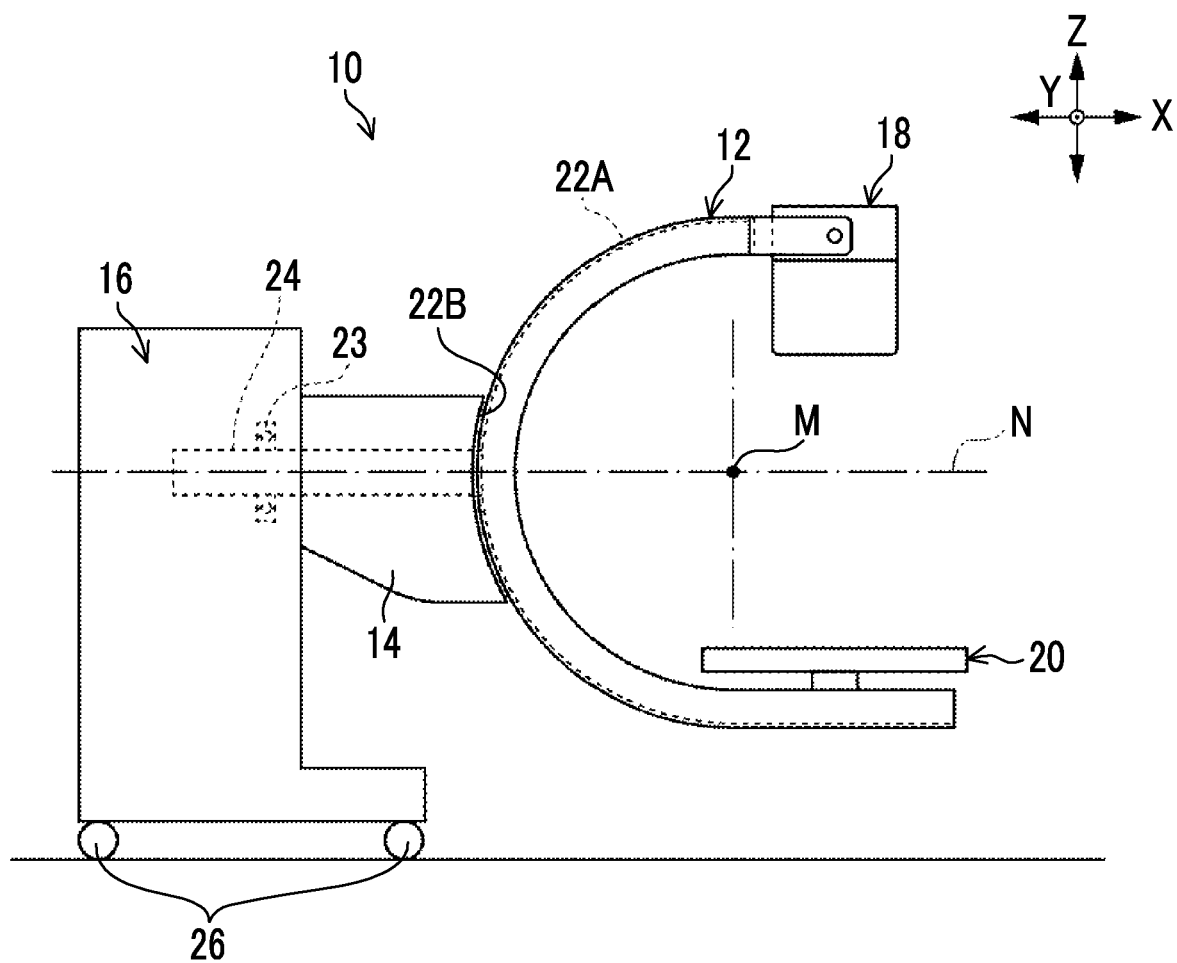
FIG. 2A is a side view illustrating the radiography apparatus according to the first embodiment.

As illustrated in FIG. 2A, the arm 12 is rotatable on an axis line M (an axis line parallel to the Y axis) with respect to a track portion 22B that is provided on the connection portion 14 constituting the support portion. Further, the arm 12 is rotatable about an axis line N (an axis line parallel to the X axis) with respect to a bearing portion 23 that is provided in the main body portion 16 constituting the support portion.

Figure 6:
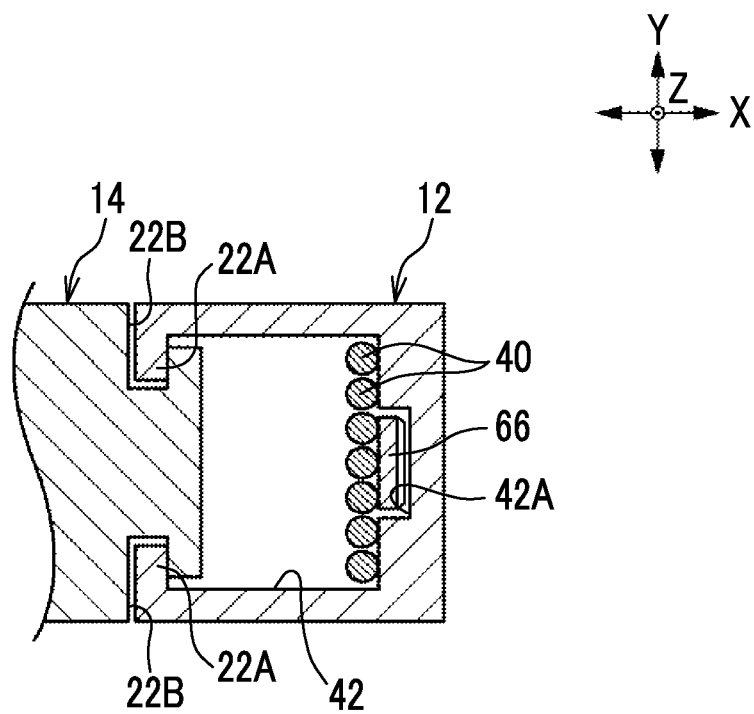
FIG. 6 is a cross-sectional view taken along the line A-A of FIG. 5.

Specifically, the track portion 22B has an arc shape that has the same radius as the arc of the arm 12. Moreover, a fitting portion 22A that is fitted to the track portion 22B is provided in an outer peripheral surface of the arm 12. The fitting portion 22A has an arc shape following the shape of the arm 12. As illustrated in FIG. 6, the track portion 22B has, for example, a groove shape, and the fitting portion 22A having a protruding shape is fitted to the track portion 22B. In addition, a roller (not illustrated) that assists the sliding of the fitting portion 22A with respect to the track portion 22B is interposed between the track portion 22B and the fitting portion 22A.

As illustrated in FIG. 2A, the fitting portion 22A formed in the arm 12 slides along the track portion 22B formed on the connection portion 14. Therefore, the arm 12 can be orbitally rotated about the axis line M at the center of the arc of the arm 12 as a rotation center with respect to the connection portion 14 and the main body portion 16.

Figure 2B:
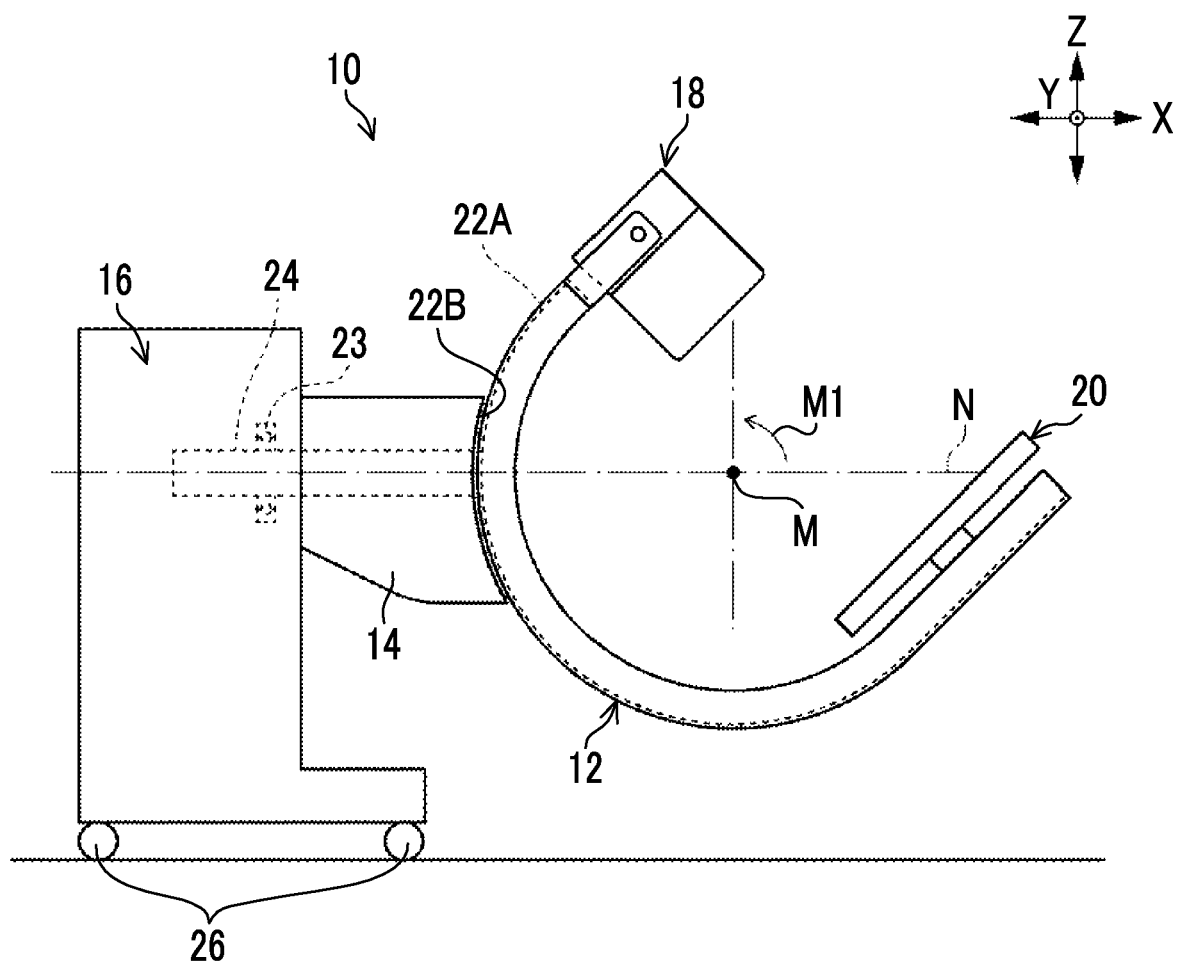
FIG. 2B is a side view illustrating a state in which an arm of the radiography apparatus illustrated in FIG. 2A is rotated in a direction of an arrow M1.
Figure 2C:
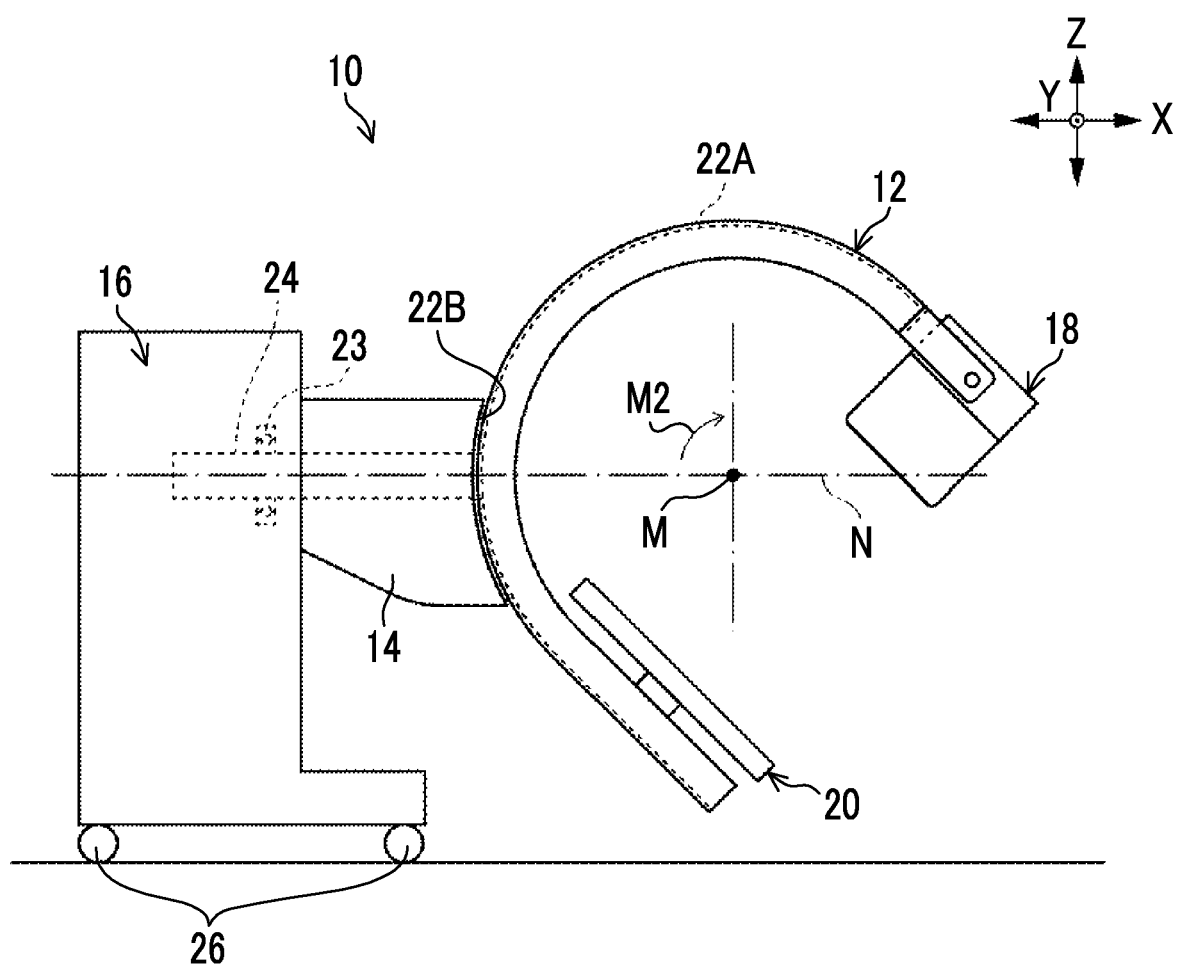
FIG. 2C is a side view illustrating a state in which the arm of the radiography apparatus illustrated in FIG. 2A is rotated in a direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, it is possible to rotate the irradiation unit 18 and the image receiving unit 20 provided at both ends of the arm 12 about the body axis (an axis parallel to the Y axis) of the subject H (see FIG. 1).

Further, as illustrated in FIG. 2A, one end of a support shaft 24 that extends in a front-rear direction (X direction) of the radiography apparatus 10 is fixed to the arm 12. The other end of the support shaft 24 is supported by the main body portion 16 through the bearing portion 23. The support shaft 24 is rotated about the axis line N with respect to the bearing portion 23 such that the arm 12 and the connection portion 14 are rotatable about the axis line N of the support shaft 24 as a rotation center with respect to the main body portion 16 as illustrated in FIGS. 3A to 3C.

Figure 3A:
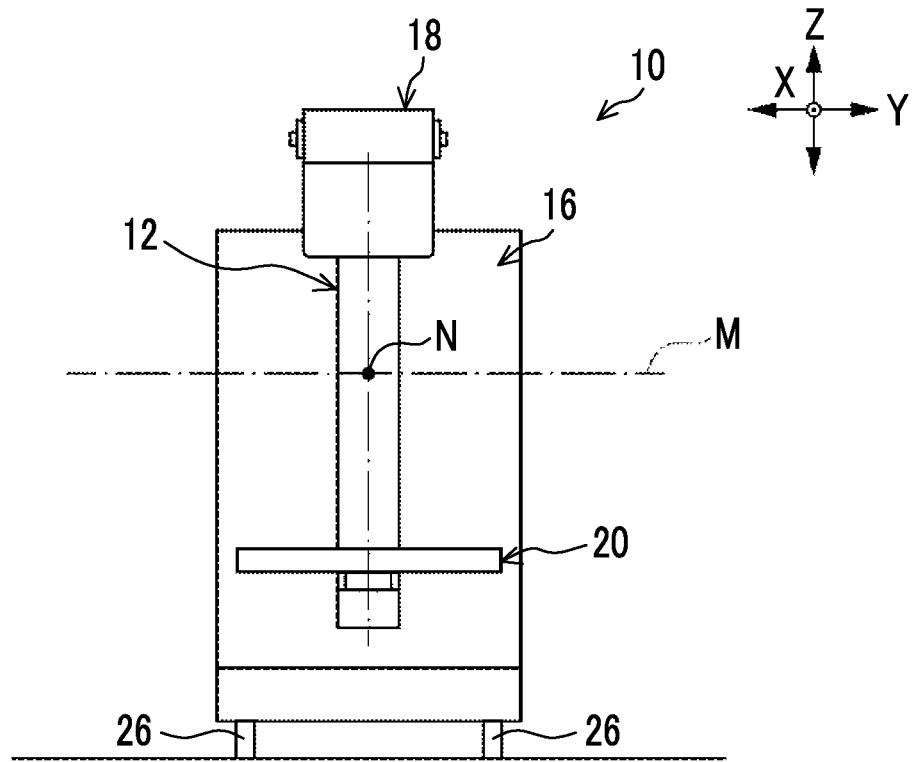
FIG. 3A is a front view illustrating the radiography apparatus according to the first embodiment.
Figure 3B:
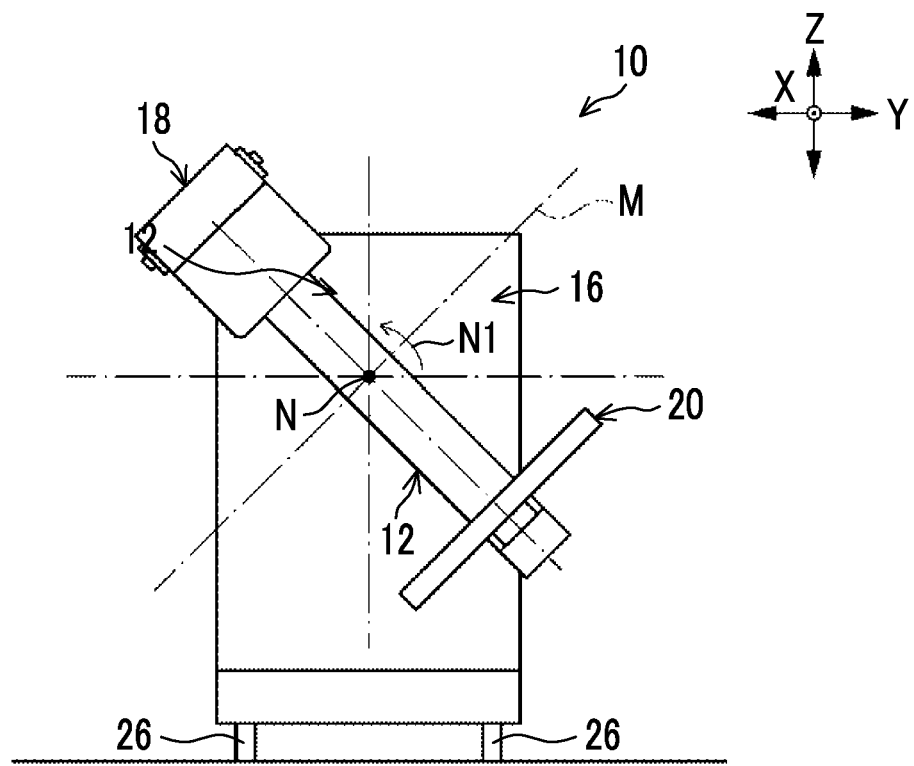
FIG. 3B is a front view illustrating a state in which the arm of the radiography apparatus illustrated in FIG. 3A is rotated in a direction of an arrow N1.
Figure 3C:
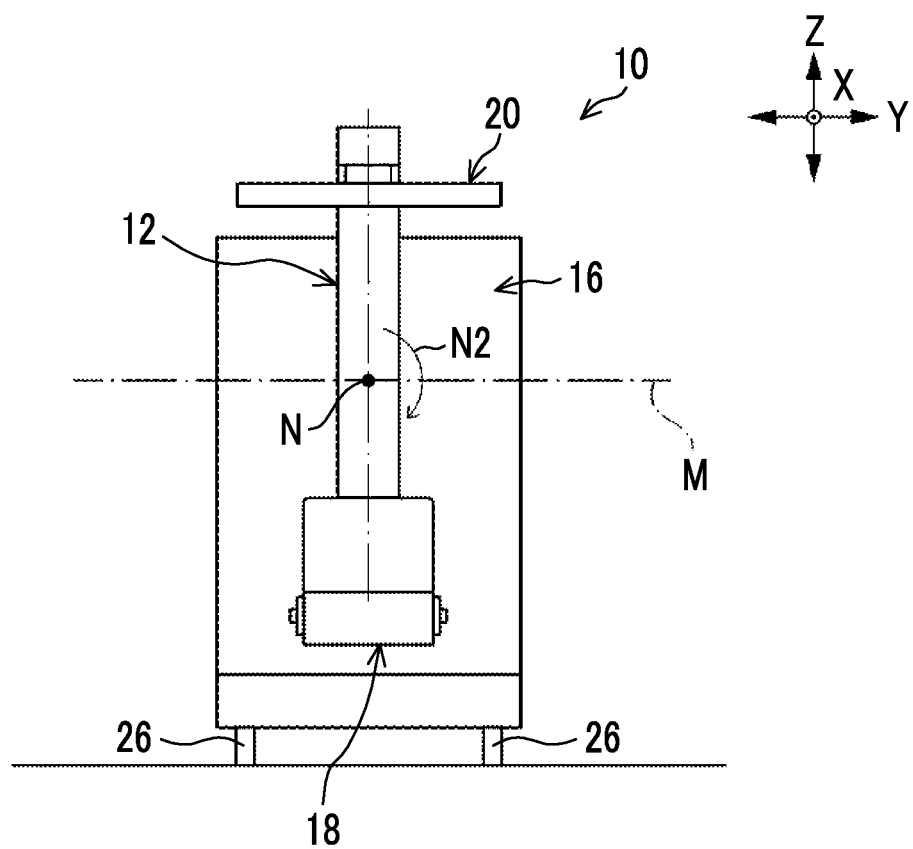
FIG. 3C is a front view illustrating a state in which the arm of the radiography apparatus illustrated in FIG. 3A is rotated 180° in a direction of an arrow N2.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction).

Here, in the posture of the arm 12 in which the irradiation unit 18 is disposed above the image receiving unit 20 as illustrated in FIG. 3A, a radiation tube 32 (see FIG. 1) included in the irradiation unit 18 is located above the subject H. Therefore, this posture is called, for example, an overtube posture. In addition, in the posture of the arm 12 in which the irradiation unit 18 is disposed below the image receiving unit 20 illustrated in FIG. 3C, the radiation tube 32 is located below the subject H. Therefore, this posture is called, for example, an undertube posture.

In the overtube posture, it is possible to increase a distance between the irradiation unit 18 and the subject H (see FIG. 1), as compared to the undertube posture. This makes it possible to image a relatively wide region in the overtube posture. Therefore, the overtube posture is mainly used to capture the still image of the subject H. On the other hand, in the undertube posture, the radiation emitted from the irradiation unit 18 is partially blocked by, for example, the bed S. Therefore, in the undertube posture, it is possible to reduce the amount of radiation exposure to, for example, a radiology technician or an operator (not illustrated) around the subject H (see FIG. 1). Therefore, the undertube posture is used for the capture of the moving image of the subject H in which radiation is continuously emitted.

(Configuration of Main Body Portion)

As illustrated in FIG. 1, a plurality of casters 26 are attached to a lower part of the main body portion 16 of the radiography apparatus 10, and the operator can push the radiography apparatus 10 with hands to move the radiography apparatus 10 into, for example, an operating room or a hospital ward. That is, the radiography apparatus 10 according to this embodiment is a mobile type.

Further, the main body portion 16 includes a control unit 28 that controls each unit of the radiography apparatus 10, such as the irradiation unit 18, and an operation panel 30 that is, for example, a touch panel type. Furthermore, the configuration of the control unit 28 will be described in detail below.

The operation panel 30 functions as an operation unit that inputs an operation instruction to each unit of the radiography apparatus 10, such as the irradiation unit 18, to operate each unit and a display unit that displays various kinds of information, such as a warning message and a radiographic image output from the image receiving unit 20. In addition, the main body portion 16 comprises various switches (not illustrated) including, for example, a power switch of the radiography apparatus 10, a power supply circuit that supplies power to each unit of the radiography apparatus 10, a battery, and the like.

(Configuration of Irradiation Unit)

The irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is a focus where radiation is emitted.

In addition, the irradiation field limiter 34 is provided below the radiation source 31. The irradiation field limiter 34 (also referred to as a collimator or the like) has a rectangular irradiation opening 34A. The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates (not illustrated) that shield radiation. In each of the four shielding plates, each side corresponds to each side of the irradiation opening 34A and defines the irradiation opening 34A. The position of the shielding plates is changed to adjust the opening area of the irradiation opening 34A, and the irradiation field of the radiation emitted from the irradiation unit 18 is changed.

Further, the irradiation unit 18 can be rotated about an axis line of a rotation shaft 36 that extends in the width direction (the Y direction in FIG. 1) of the radiography apparatus 10 as a rotation center with respect to the arm 12. Specifically, a pair of attachment plates 38 (only one attachment plate is illustrated in FIG. 1) are fixed to one end of the arm 12.

The pair of attachment plates 38 are disposed such that both sides of the irradiation unit 18 in the width direction are interposed therebetween and are connected to both side surfaces of the irradiation unit 18 in the width direction. Each rotation shaft 36 protrudes from each side surface of the irradiation unit 18 which faces each attachment plate 38. The rotation shafts 36 are supported by the pair of attachment plates 38 through bearing portions (not illustrated). Therefore, the irradiation unit 18 can be rotated about the axis line of the rotation shaft 36 as the rotation center with respect to the attachment plates 38, and the orientation of the irradiation opening 34A of the irradiation unit 18 can be changed in the front-rear direction of the arm 12. The orientation of the irradiation opening 34A can be changed to change the irradiation direction of radiation.

Further, the irradiation unit 18 is connected to one end of each of a plurality of cables 40 including a signal line for transmitting a control signal and a power line for supplying power. As illustrated in FIG. 6, the cables 40 are provided in a hollow portion 42 that is formed in the arm 12 and extend along the arm 12. Furthermore, the other end of the cable 40 is connected to, for example, the control unit 28 and a power supply circuit (not illustrated) of the main body portion 16 illustrated in FIG. 1.

(Configuration of Image Receiving Unit)

As illustrated in FIG. 1, the image receiving unit 20 is provided at the other end of the arm 12 which is a position facing the irradiation unit 18. In this embodiment, in the image receiving unit 20, a detector is provided in a housing to be undetachable. The image receiving unit 20 has an image receiving surface 20A that receives the radiation which has been emitted from the irradiation unit 18 and then transmitted through the subject H. The radiation carrying the information of the subject H is incident on the image receiving surface 20A.

The detector receives the radiation which has been emitted from the irradiation unit 18 and then transmitted through the subject H to detect a radiographic image of the subject H. The detector is, for example, a flat panel detector (FPD) of a digital radiography (DR) type.

The FPD has a detection surface in which a plurality of pixels are two-dimensionally arranged and a thin film transistor (TFT) panel (not illustrated) for driving the pixels. The radiation is incident on the detection surface of the detector through the image receiving surface 20A. The detector converts the incident radiation into an electric signal and outputs a radiographic image indicating the subject H on the basis of the converted electric signal. For example, the detector is an indirect conversion type that converts radiation into visible light using a scintillator and converts the converted visible light into an electric signal. In addition, the detector may be a direct conversion type that directly converts radiation into an electric signal. Further, the image receiving unit 20 may have, for example, a configuration in which an image intensifier (II) and a camera are combined other than the configuration using the FPD.

Furthermore, as illustrated in FIGS. 4A and 4B, the image receiving unit 20 is a portable type that is detachably attached to the arm 12. The portable image receiving unit 20 is called, for example, an electronic cassette. Specifically, the image receiving unit 20 is detachably attached to a base 44 that is provided at the other end of the arm 12.

Specifically, the base 44 is provided on an upper surface of the other end of the arm 12, and a fitting protruding portion 46 is provided uprightly on the base 44. Each of the base 44 and the fitting protruding portion 46 has a rectangular parallelepiped shape, and the width (length in the Y direction) of the fitting protruding portion 46 is smaller than the width (length in the Y direction) of the base 44.

The image receiving unit 20 has a flat rectangular parallelepiped shape. A fitting recessed portion 48 that is fitted to the fitting protruding portion 46 is formed in a lower surface of the image receiving unit 20. The fitting recessed portion 48 has a rectangular parallelepiped shape, and the length (length in the Y direction in FIG. 4A) of the fitting recessed portion 48 in a lateral direction is larger than the width of the fitting protruding portion 46 and is smaller than the width of the base 44. Further, the height of the fitting recessed portion 48 is substantially equal to the height of the fitting protruding portion 46.

Furthermore, the length (length in the X direction in FIG. 4A) of the fitting recessed portion 48 in a longitudinal direction is larger than the length (length in the X direction) of the base 44 and the fitting protruding portion 46. One end of the fitting recessed portion 48 in the longitudinal direction extends to one side surface of the image receiving unit 20. Since one end of the fitting recessed portion 48 is located on one side surface of the image receiving unit 20, a portion of the one side surface of the image receiving unit 20 is open.

In a case in which the image receiving unit 20 is attached to the arm 12, the image receiving unit 20 is moved in the horizontal direction (X direction) such that the fitting protruding portion 46 provided uprightly on the base 44 is inserted into the fitting recessed portion 48 through the opening formed in one side surface of the image receiving unit 20. Then, the lower surface of the image receiving unit 20 comes into contact with the upper surface of the base 44 in a state in which the fitting protruding portion 46 is fitted to the fitting recessed portion 48.

Here, a pair of positioning pins 50 that protrude into the fitting recessed portion 48 are provided on the other end surface of the fitting recessed portion 48 in the longitudinal direction. A pair of pin holes 52 into which the positioning pins 50 are inserted are formed in one side surface of the fitting protruding portion 46 which faces the other end surface of the fitting recessed portion 48 in the longitudinal direction in a case in which the fitting protruding portion 46 is fitted to the fitting recessed portion 48. In a case in which the fitting recessed portion 48 of the image receiving unit 20 is fitted to the fitting protruding portion 46, the pair of positioning pins 50 are inserted into the pair of pin holes 52 such that the image receiving unit 20 is positioned and attached to the base 44, that is, the other end of the arm 12.

In addition, a through-hole 54 that extends in the vertical direction (Z direction) is formed in the upper surface of the base 44, and a solenoid 56 is provided below the through-hole 54 at the other end of the arm 12. Then, an insertion hole 58 having substantially the same diameter as the through-hole 54 is formed in the lower surface of the image receiving unit 20. Here, the insertion hole 58 of the image receiving unit 20 is formed at a position where the insertion hole 58 communicates with the through-hole 54 of the base 44 in a case in which the image receiving unit 20 is positioned and attached to the base 44.

The solenoid 56 comprises a movable iron core 56A that is inserted into the through-hole 54. The movable iron core 56A can be expanded and contracted by switching the solenoid 56 between an energized state and a non-energized state.

Specifically, in a case in which the solenoid 56 is energized, the movable iron core 56A is attracted to a main body of the solenoid 56, and a tip of the movable iron core 56A is located in the through-hole 54 of the base 44 as illustrated in FIG. 4A. In this state, since the movable iron core 56A is not inserted into the insertion hole 58 of the image receiving unit 20, the image receiving unit 20 can be attached to and detached from the base 44, that is, the arm 12.

On the other hand, in a state in which the insertion hole 58 of the image receiving unit 20 and the through-hole 54 of the base 44 communicate with each other, that is, in a state in which the image receiving unit 20 is positioned and attached to the other end of the arm 12, the movable iron core 56A can be inserted into the insertion hole 58 of the image receiving unit 20 as illustrated in FIG. 4B.

Therefore, in a case in which the solenoid 56 is de-energized in a state in which the image receiving unit 20 is positioned and attached to the other end of the arm 12, the tip of the movable iron core 56A is inserted into the insertion hole 58 and reaches the image receiving unit 20. In this state, since the movable iron core 56A of the solenoid 56 is also inserted into the insertion hole 58 of the image receiving unit 20, the detachment of the image receiving unit 20 from the base 44, that is, the arm 12 is restricted. As described above, the solenoid 56 constitutes an attachment and detachment restriction mechanism that restricts the inadvertent attachment and detachment of the image receiving unit 20 to and from the arm 12 in a state in which the image receiving unit 20 is attached to the arm 12.

Further, the base 44 is provided with a photo sensor 60 as a first attachment and detachment detection unit that detects whether or not the image receiving unit 20 is detached from the arm 12. The photo sensor 60 is, for example, a reflective sensor in which a light emitting window through which a light emitting element (not illustrated) emits light and a light receiving window through which a light receiving element (not illustrated) receives light are arranged on the same surface. In the photo sensor 60, in a state in which the image receiving unit 20 is not attached to the base 44, the light emitting window and the light receiving window are exposed to the outside. On the other hand, the photo sensor 60 is provided at a position where the light emitting window and the light receiving window are covered by the image receiving unit 20 in a state in which the image receiving unit 20 is attached to the base 44.

For example, the photo sensor 60 according to this embodiment is disposed on the base 44 in a posture facing the upper surface in FIG. 4A. In the photo sensor 60, in a state in which the image receiving unit 20 is attached to the base 44, the light emitted from the light emitting window is reflected by the image receiving unit 20. Therefore, the amount of light received through the light receiving window increases. On the other hand, in a state in which the image receiving unit 20 is detached from the base 44 and is retracted from the front surfaces of the light emitting window and the light receiving window, light is not reflected from the image receiving unit 20. Therefore, the amount of light received through the light receiving window is reduced.

As described above, the photo sensor 60 can detect a change in the light which has been emitted from the light emitting window and then received by the light receiving element to detect whether or not the image receiving unit 20 is detached from the arm 12.

The photo sensor 60 outputs an on signal to the control unit 28 as a detection signal in a state in which it is detected that the image receiving unit 20 is attached to the arm 12. Further, the photo sensor 60 outputs an off signal to the control unit 28 as a detection signal in a state in which it is detected that the image receiving unit 20 is detached from the arm 12.

In addition, the portable image receiving unit 20 has, for example, a battery and a wireless communication unit which are not illustrated and can wirelessly communicate with the control unit 28 (see FIG. 1) provided in the main body portion 16. In a case in which the wireless communication unit is used, the image receiving unit 20 is driven by power from the battery and can be used in a so-called cableless manner. Therefore, the image receiving unit 20 can be used in a state in which it is detached from the arm 12.

On the other hand, in a case in which the image receiving unit 20 is attached to the arm 12, a terminal 62A that is provided in the fitting recessed portion 48 of the image receiving unit 20 and a terminal 62B that is provided in the fitting protruding portion 46 of the arm 12 illustrated in FIG. 4A come into contact with each other, and the image receiving unit 20 and the base 44 are electrically connected to each other.

Further, the base 44 is connected to, for example, the control unit 28 and a power supply circuit (not illustrated) of the main body portion 16 by a cable (not illustrated) including a signal line for transmitting a control signal and a power line for supplying power. Therefore, in a state in which the image receiving unit 20 is attached to the arm 12, the image receiving unit 20 is connected to, for example, the control unit 28 and the power supply circuit (not illustrated) through a cable (not illustrated).

(Configuration of First Locking Mechanism)

Figure 5:
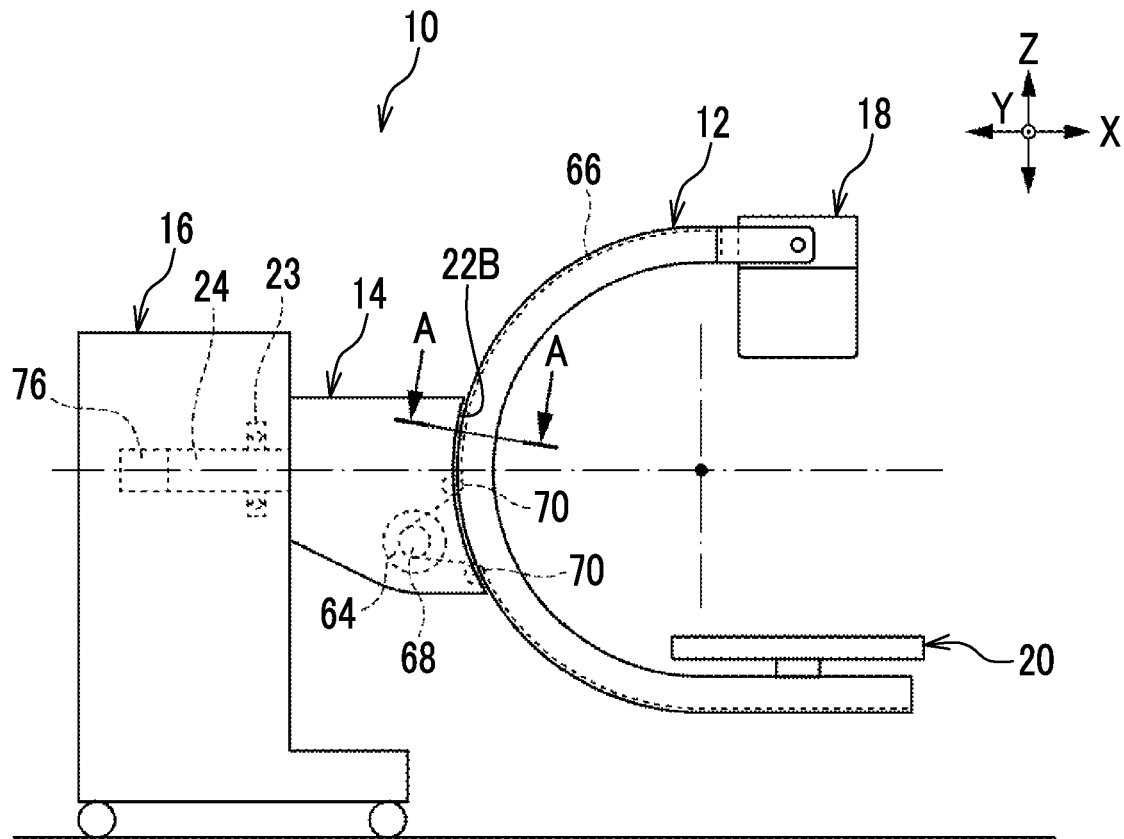
FIG. 5 is an overall side view illustrating a locking mechanism of the radiography apparatus according to the first embodiment.

As illustrated in FIG. 5, the radiography apparatus 10 is provided with a first locking mechanism 64 and a second locking mechanism 76 as a locking mechanism for locking the rotation of the arm 12. The first locking mechanism 64 is provided in the connection portion 14 and locks the orbital rotation of the arm 12, that is, the rotation of the arm 12 with respect to the track portion 22B.

Specifically, both ends of a timing belt 66 are fixed to both ends of the arm 12, respectively. The arm 12 is a hollow cylindrical body. As illustrated in FIG. 6, the timing belt 66 and the cables 40 are provided in the hollow portion 42 of the arm 12. In the hollow portion 42, a groove 42A that extends along the arc of the arm 12 is formed in the front inner surface of the arm 12. The timing belt 66 extends along the arc of the arm 12 in a state in which it is accommodated in the groove 42A. Therefore, it is possible to suppress interference between the cables 40 and the timing belt 66 in the hollow portion 42.

Figure 7:
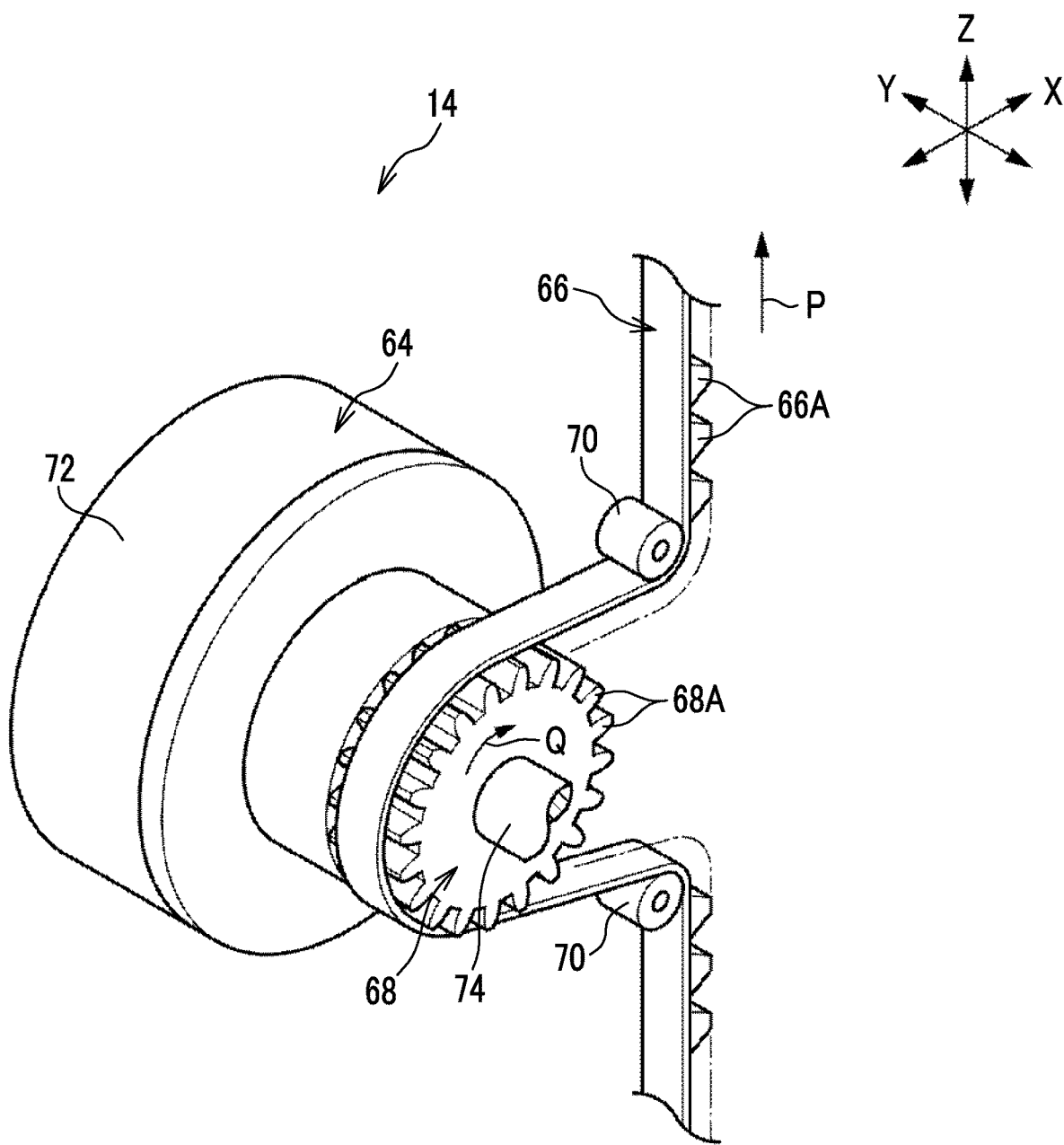
FIG. 7 is a perspective view illustrating a first locking mechanism of the radiography apparatus according to the first embodiment.

Further, the timing belt 66 is wound around a timing pulley 68 that is provided in the connection portion 14 between one end and the other end of the arm 12. As illustrated in FIG. 7, a plurality of teeth 66A are formed on the timing belt 66, and a plurality of grooves 68A are formed in an outer peripheral surface of the timing pulley 68. The teeth 66A of the timing belt 66 are engaged with the grooves 68A of the timing pulley 68 such that the timing belt 66 and the timing pulley 68 are operatively associated with each other.

Further, idlers 70 are provided on the upper side of the timing pulley 68 in the vertical direction (Z direction) and on the lower side of the timing pulley 68 in the vertical direction (Z direction) in the connection portion 14. The timing belt 66 is guided by a pair of idlers 70 while being kept at a predetermined tension and is wound around the timing pulley 68.

In a case in which the arm 12 is orbitally rotated with respect to the track portion 22B (see FIG. 5), the timing belt 66 follows the movement of the arm 12. For example, in a case in which one end of the arm 12 is moved in a direction in which it becomes further away from the connection portion 14 (track portion 22B), the timing belt 66 is moved in the direction of an arrow P in FIG. 7, that is, in a direction in which the one end becomes further away from the connection portion 14. In this case, the timing pulley 68 engaged with the timing belt 66 is also rotated in the direction of an arrow Q (clockwise in FIG. 7), following the movement of the timing belt 66.

Here, in this embodiment, the first locking mechanism 64 is connected to the timing pulley 68. The first locking mechanism 64 is, for example, a non-excited electromagnetic brake, locks rotation in a case in which it is not energized, and releases the lock of the rotation in a case in which it is energized. Since the non-excited electromagnetic brake is used as the first locking mechanism 64, the rotation of the arm 12 is locked in a case in which the first locking mechanism 64 is de-energized due to, for example, a power failure. Therefore, it is possible to suppress the inadvertent rotation of the arm 12.

Specifically, the first locking mechanism 64 comprises a housing 72 in which an electromagnet (not illustrated) is provided and a rotation shaft 74 which is attached to the housing 72 through a rotor (not illustrated) provided in the housing 72. The housing 72 is fixed to the connection portion 14 such that it is not rotatable. On the other hand, the rotor and the rotation shaft 74 is supported by the connection portion 14 through a bearing portion (not illustrated) so as to be rotatable. Further, the timing pulley 68 is fixed to the rotation shaft 74 so as to be coaxially rotatable.

The electromagnet and the rotor are disposed around the rotation shaft 74. The electromagnet and the rotor face each other in the axial direction of the rotation shaft 74, which is not illustrated. Further, in the housing 72, a movable iron piece that is movable in the axial direction of the rotation shaft 74 is provided between the electromagnet and the rotor. The movable iron piece is disposed so as to be separated from the electromagnet and is biased toward the rotor by a biasing member (not illustrated) to press the rotor against an inner wall surface of the housing 72.

In a case in which the first locking mechanism 64 is not energized, the rotor is pressed against the inner wall surface of the housing 72 by the movable iron piece and is closely attached to the inner wall surface. Therefore, the rotation of the rotor with respect to the housing 72 is locked. Then, since the rotation of the rotor with respect to the housing 72 is locked, the rotation of the rotation shaft 74 fixed to the rotor and the timing pulley 68 fixed to the rotation shaft 74 is locked. Furthermore, the movement of the timing belt 66 engaged with the timing pulley 68 is also locked.

Both ends of the timing belt 66 are fixed to both ends of the arm 12. Therefore, the movement of the timing belt 66 is locked to lock the orbital rotation of the arm 12 with respect to the track portion 22B (see FIG. 5).

On the other hand, in a case in which the first locking mechanism 64 is energized, a magnetic force is generated in the electromagnet provided in the housing 72, and the movable iron piece is attracted to the electromagnet against the biasing force of the biasing member. Therefore, the pressing of the rotor against the inner wall surface of the housing 72 by the movable iron piece is released, and the rotor can be rotated with respect to the housing 72. That is, the lock of the rotation of the rotor is released.

In addition, in a case in which the lock of the rotation of the rotor is released, the lock of the rotation of the rotation shaft 74 and the timing pulley 68 is also released. Further, the timing belt 66 engaged with the timing pulley 68 can be moved. Therefore, the lock of the orbital rotation of the arm 12 with respect to the track portion 22B (see FIG. 5) is released.

(Configuration of Second Locking Mechanism)

Figure 8:
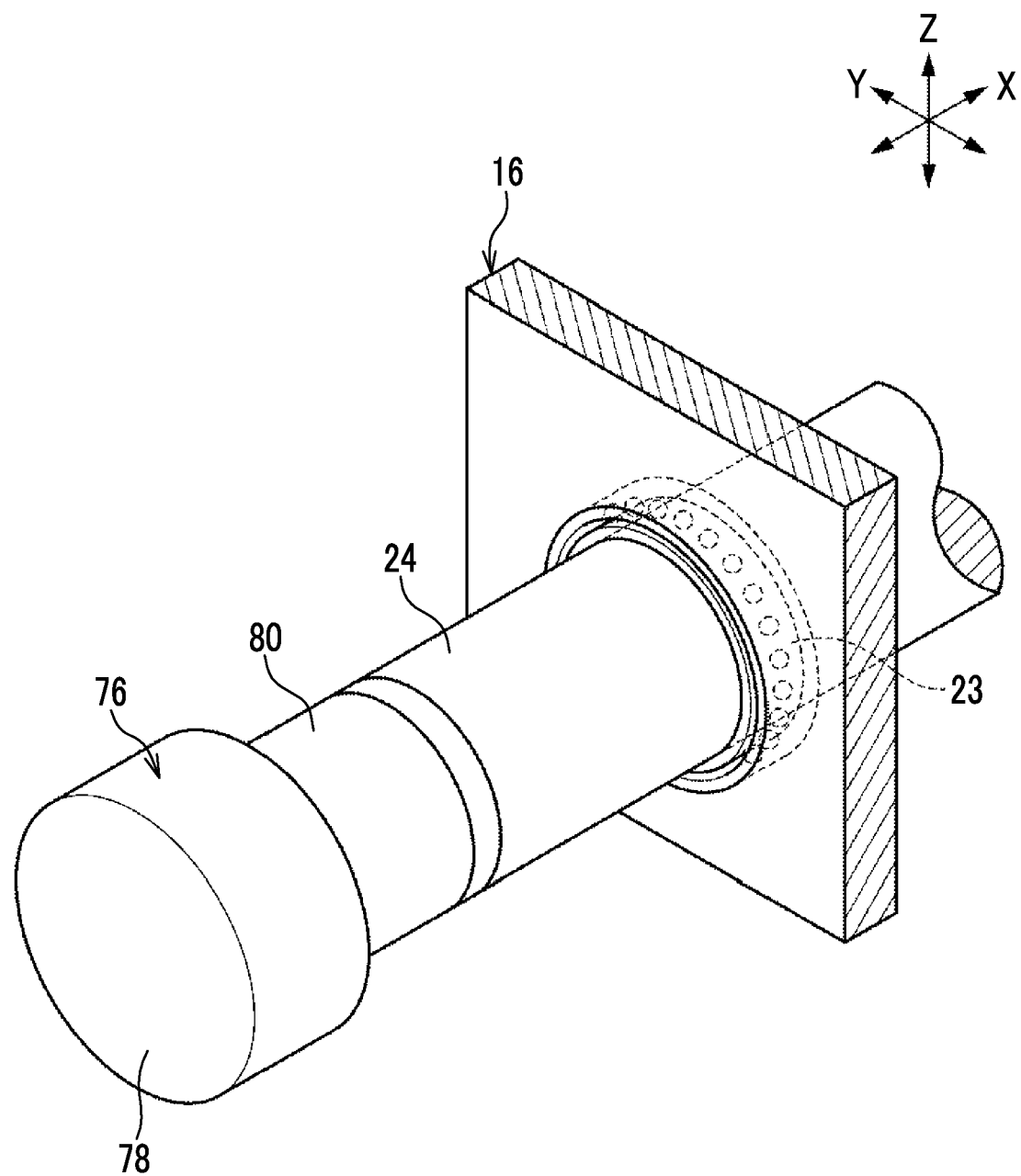
FIG. 8 is a perspective view illustrating a second locking mechanism of the radiography apparatus according to the first embodiment.

As illustrated in FIG. 5, the second locking mechanism 76 is provided in the main body portion 16 and locks the axial rotation of the arm 12, that is, the rotation of the arm 12 with respect to the bearing portion 23. Specifically, as illustrated in FIG. 8, the second locking mechanism 76 is attached to the other end of the support shaft 24.

The second locking mechanism 76 is, for example, a non-excited electromagnetic brake, similarly to the first locking mechanism 64. The second locking mechanism 76 comprises a housing 78 that is fixed to the main body portion 16 such that it is not rotatable and a rotation shaft 80 that is attached to the housing 78 through a rotor (not illustrated) so as to be rotatable. The support shaft 24 is fixed to the rotation shaft 80 so as to be coaxially rotatable.

In a case in which the second locking mechanism 76 is not energized, the rotor is pressed against an inner wall surface of the housing 78 by a movable iron piece (not illustrated) and is closely attached to the inner wall surface. Therefore, the rotation of the rotor with respect to the housing 78 is locked. Then, the rotation of the rotor with respect to the housing 78 is locked to lock the rotation of the rotation shaft 80 fixed to the rotor and the support shaft 24 fixed to the rotation shaft 80. The rotation of the support shaft 24 is locked to lock the axial rotation of the arm 12 with respect to the bearing portion 23.

On the other hand, in a case in which the second locking mechanism 76 is energized, a magnetic force is generated in an electromagnet (not illustrated) that is provided in the housing 78, and the movable iron piece (not illustrated) is attracted to the electromagnet. Therefore, the pressing of the rotor against the inner wall surface of the housing 78 by the movable iron piece is released. Then, the rotor can be rotated with respect to the housing 78. That is, the lock of the rotation of the rotor is released.

Further, in a case in which the lock of the rotation of the rotor is released, the lock of the rotation of the rotation shaft 80 and the support shaft 24 fixed to the rotation shaft 80 is also released. Therefore, the lock of the axial rotation of the arm 12 with respect to the bearing portion 23 is released.

(Configuration of Control Unit)

Figure 9:
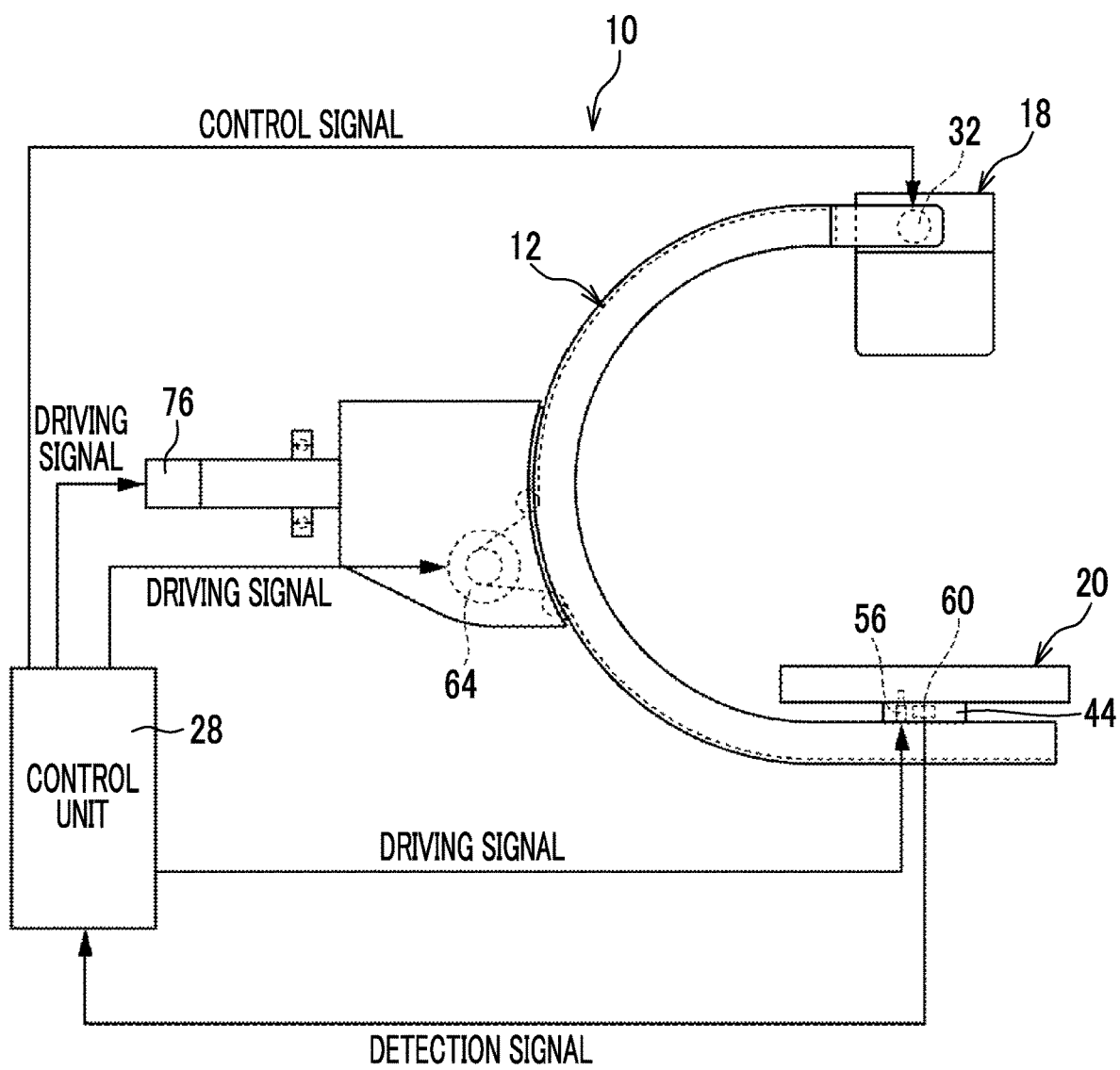
FIG. 9 is a block diagram illustrating a functional configuration of a control unit of the radiography apparatus according to the first embodiment.

As illustrated in FIG. 9, in the radiography apparatus 10, the control unit 28 provided in the main body portion 16 (see FIG. 1) transmits a control signal to the radiation tube 32 of the irradiation unit 18 to control, for example, the tube voltage, tube current, and irradiation time of radiation of the radiation tube 32. The tube voltage is controlled to control the energy of the radiation. In addition, the tube current and the irradiation time are controlled to control a radiation dose. In practice, since a high voltage is applied to the radiation tube 32, the control unit 28 controls the radiation tube 32 through a high-voltage generation device (not illustrated). In imaging, imaging conditions including, for example, the tube voltage, the tube current, and the irradiation time are set through the operation panel 30 (see FIG. 1). The control unit 28 operates the irradiation unit 18 on the basis of the set imaging conditions.

The control unit 28 directs the irradiation unit 18 to perform moving image capture irradiation in which the irradiation unit 18 continuously emits radiation such that a moving image of the subject H (see FIG. 1) can be captured. Here, the term "continuous emission of radiation" includes not only continuous emission in which radiation is continuously emitted but also so-called pulse emission in which radiation is repeatedly emitted at a preset short time interval.

In a case in which a moving image is captured, the control unit 28 operates the detector of the image receiving unit 20 in synchronization with irradiation for capturing a moving image by the irradiation unit 18. In a case in which a moving image is captured, basically, the irradiation time is not set as the imaging condition, and instructions to start and end the capture of the moving image are input through the operation panel 30. In a case in which the instruction to start the capture of a moving image is input, the control unit 28 directs the irradiation unit 18 to start the emission of radiation under preset imaging conditions. Of course, the instructions to start and end the capture of a moving image may be input by, for example, a foot switch other than the operation panel 30.

In the capture of a moving image, the detector repeats an image detection operation at a preset frame rate while the moving image capture irradiation is performed. An image output by the detector is transmitted to the control unit 28. The control unit 28 sequentially outputs the received images to a monitor (not illustrated). Therefore, the moving image of the subject H is displayed on the monitor.

In addition, the control unit 28 directs the irradiation unit 18 to perform still image capture irradiation in which the irradiation unit 18 emits radiation for a shorter time than in the moving image capture irradiation such that a still image of the subject H (see FIG. 1) can be captured.

In the capture of a still image, the control unit 28 operates the detector of the image receiving unit 20 in synchronization with the irradiation timing in the still image capture irradiation by the irradiation unit 18. For example, an instruction to capture a still image is input through an irradiation switch (not illustrated) that is connected to the control unit 28. In the capture of a still image, the irradiation time is, for example, in the order of several tens of milliseconds to several hundreds of milliseconds. In a case in which an instruction to capture a still image is input, the control unit 28 operates the irradiation unit 18 on the basis of preset imaging conditions. In a case in which a still image is captured, the irradiation time is set in the imaging conditions. Therefore, in a case in which the set irradiation time has elapsed, the irradiation of the irradiation unit 18 ends.

In a case in which the irradiation ends, the detector starts to output the detected image. The image output by the detector is transmitted to the control unit 28. The control unit 28 stores data of the still image in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after imaging.

Further, the control unit 28 controls the solenoid 56. That is, in a case in which an operation of derestricting attachment and detachment is performed through the operation panel 30 (see FIG. 1) in a state in which the attachment and detachment of the image receiving unit 20 to and from the arm 12 is restricted by the solenoid 56, the control unit 28 transmits a driving signal to the solenoid 56 to energize the solenoid 56. Then, the movable iron core 56A (see FIG. 4B) is attracted by the solenoid 56, and the image receiving unit 20 is detachable from the arm 12.

On the other hand, in a case in which an instruction to restrict the attachment and detachment of the image receiving unit 20 is input through the operation panel 30 (see FIG. 1), the control unit 28 de-energizes the solenoid 56. In this case, in the state in which the image receiving unit 20 is attached to the arm 12, the insertion hole 58 of the image receiving unit 20 illustrated in FIG. 4B and the through-hole 54 of the base 44 communicate with each other. Therefore, the movable iron core 56A is inserted into the insertion hole 58 of the image receiving unit 20 to restrict the attachment and detachment of the image receiving unit 20 to and from the arm 12.

As described above, the control unit 28 controls the energization of the solenoid 56 to perform switching between a state in which the attachment and detachment of the image receiving unit 20 to and from the arm 12 is permitted and a state in which the attachment and detachment of the image receiving unit 20 to and from the arm 12 is restricted. In addition, in a case in which the image receiving unit 20 is not attached to the arm 12, that is, the insertion hole 58 of the image receiving unit 20 illustrated in FIG. 4B and the through-hole 54 of the base 44 do not communicate with each other, it is difficult to insert the movable iron core 56A into the insertion hole 58 even though an instruction to restrict the attachment and detachment of the image receiving unit 20 is input. Therefore, the attachment and detachment of the image receiving unit 20 to and from the arm 12 is not restricted.

Further, the control unit 28 determines whether or not the image receiving unit 20 is detached from the arm 12 on the basis of a detection signal from the photo sensor 60 provided in the arm 12. That is, in a case in which the image receiving unit 20 is attached to the arm 12 as illustrated in FIG. 4B, the control unit 28 receives an on signal as the detection signal from the photo sensor 60. The control unit 28 determines that the image receiving unit 20 is attached to the arm 12 while receiving the on signal from the photo sensor 60.

On the other hand, in a case in which the image receiving unit 20 is detached from the arm 12 as illustrated in FIG. 4A, the control unit 28 receives an off signal as the detection signal from the photo sensor 60. The control unit 28 determines that the image receiving unit 20 is detached from the arm 12 while receiving the off signal from the photo sensor 60.

Further, the control unit 28 controls the first locking mechanism 64 in response to an operation instruction from the operation panel 30. That is, in a case in which an unlock instruction to turn off the lock of the rotation is input through the operation panel 30, the control unit 28 transmits a driving signal to the first locking mechanism 64 to energize the first locking mechanism 64. Then, the lock of the rotation of the rotation shaft 74 and the timing pulley 68 with respect to the housing 72 illustrated in FIG. 7 is released to unlock the orbital rotation of the arm 12 with respect to the track portion 22B.

On the other hand, in a case in which a lock instruction to turn on the lock of the rotation is input through the operation panel 30, the control unit 28 de-energizes the first locking mechanism 64. Then, the rotation of the rotation shaft 74 and the timing pulley 68 with respect to the housing 72 illustrated in FIG. 7 is locked to lock the orbital rotation of the arm 12 with respect to the track portion 22B.

Similarly, the control unit 28 controls the second locking mechanism 76 in response to an operation signal from the operation panel 30. That is, in a case in which an unlock instruction to turn off the lock of the rotation is input through the operation panel 30, the control unit 28 transmits a driving signal to the second locking mechanism 76 to energize the second locking mechanism 76. Then, the lock of the rotation of the rotation shaft 80 and the support shaft 24 with respect to the housing 78 illustrated in FIG. 8 is released to unlock the axial rotation of the arm 12 with respect to the bearing portion 23.

On the other hand, in a case in which the lock instruction to turn on the lock of the rotation is input through the operation panel 30, the control unit 28 de-energizes the second locking mechanism 76. Then, the lock of the rotation of the rotation shaft 80 and the support shaft 24 with respect to the housing 78 illustrated in FIG. 8 is released to unlock the axial rotation of the arm 12 with respect to the bearing portion 23.

(Method for Controlling Radiography Apparatus)

Next, a method for controlling the radiography apparatus 10 according to this embodiment will be described with reference to a flowchart illustrated in FIG. 10.

First, in Step S500, in a case in which the radiography apparatus 10 is turned on by the operation of a power switch (not illustrated) (Y in Step S500), the control unit 28 starts to control the radiography apparatus 10. In a case in which the control by the control unit 28 is started, it is possible to receive the input of the imaging conditions through the operation panel 30. In addition, the first locking mechanism 64 and the second locking mechanism 76 according to this embodiment adopt the non-excited electromagnetic brakes. Therefore, the rotation of the arm 12 is locked in a state in which the radiography apparatus 10 is turned off. Therefore, in this embodiment, the rotation of the arm 12 is locked in a state in which the radiography apparatus 10 is started.

In Step S502, the control unit 28 determines whether or not an unlock operation for releasing the lock of the rotation of the arm 12 has been performed. In a case in which there is no unlock instruction in Step S502 (N in Step S502), the process proceeds to Step S504, and the rotation-locked state of the arm 12 is maintained. That is, the unlocking of the rotation of the arm 12 is prohibited. Then, the process returns to Step S514.

In a case in which there is an unlock instruction in Step S502 (Y in Step S502), the control unit 28 determines whether or not the image receiving unit 20 is attached to the arm 12 (Step S506).

In a case in which the control unit 28 determines in Step S506 that the image receiving unit 20 is not attached to the arm 12 (N in Step S506), the process proceeds to Step S504, and the rotation-locked state of the arm 12 is maintained. That is, the unlocking of the rotation of the arm 12 is prohibited. Then, the process returns to Step S514.

In a case in which the control unit 28 determines in Step S506 that the image receiving unit 20 is attached to the arm 12 (Y in Step S506), the control unit 28 energizes the first locking mechanism 64 and the second locking mechanism 76 to release the lock of the rotation of the arm 12 (Step S508).

After releasing the lock of the rotation of the arm 12 in Step S508, the control unit 28 waits until a lock operation for locking the rotation of the arm 12 is performed (Step S510). Then, in a case in which there is a lock instruction (Step S510 is Y), the control unit 28 de-energizes the first locking mechanism 64 and the second locking mechanism 76 to lock the rotation of the arm 12 (Step S512).

In Step S514, the control unit 28 determines whether or not the radiography apparatus 10 has been turned off by the operation of the power switch (not illustrated) by the operator. Then, in a case in which the radiography apparatus 10 has not been turned off (N in Step S514), the process returns to Step S502. On the other hand, in a case in which the radiography apparatus 10 has been turned off (Y in Step S514), the control unit 28 ends the control of the radiography apparatus 10.

Figure 10:
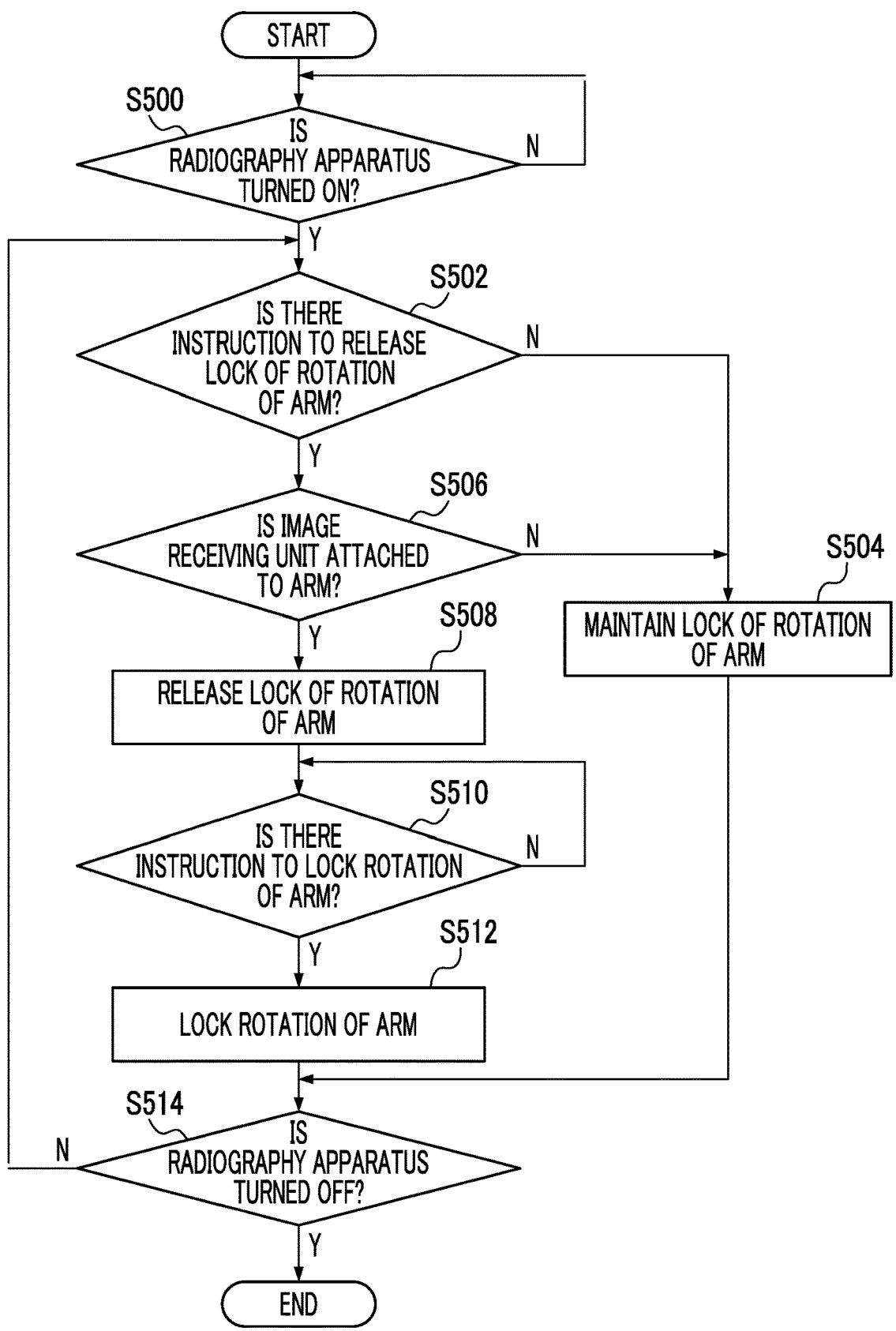
FIG. 10 is a flowchart illustrating a processing procedure of the control unit of the radiography apparatus according to the first embodiment.

In addition, the radiography apparatus 10 may be turned off in a state in which the lock of the rotation of the arm 12 is released in Step S508, which is not illustrated in the flowchart of FIG. 10. In this case, the rotation of the arm 12 is locked by turning off the radiography apparatus 10 to de-energize the first locking mechanism 64 and the second locking mechanism 76 even though the lock instruction is not input through the operation panel 30.

(Operation and Effect)

According to the radiography apparatus 10 of this embodiment, the connection portion 14 is provided with the first locking mechanism 64 that locks the orbital rotation of the arm 12 with respect to the track portion 22B. In addition, the main body portion 16 is provided with the second locking mechanism 76 that locks the axial rotation of the arm 12 with respect to the bearing portion 23.

Further, in the arm 12, the base 44 to which the image receiving unit 20 is attached is provided with the photo sensor 60 as an example of the first attachment and detachment detection unit. The photo sensor 60 can detect whether or not the image receiving unit 20 is detached from the arm 12.

Furthermore, in this embodiment, the control unit 28 of the radiography apparatus 10 performs control to prohibit the unlocking of the rotation of the arm 12 even in a case in which the unlock operation for releasing the lock of the rotation of the arm 12 by the first locking mechanism 64 and the second locking mechanism 76 is performed in a state in which the image receiving unit 20 is detached from the arm 12. Therefore, it is possible to suppress the inadvertent rotation of the arm 12 in a case in which the image receiving unit 20 is detached, without using a complicated mechanism such as a weight balance adjustment mechanism used in the related art.

In the radiography apparatus 10 according to this embodiment, two locking mechanisms, that is, the first locking mechanism 64 that locks the orbital rotation of the arm 12 and the second locking mechanism 76 that locks the axial rotation of the arm 12, are provided as the locking mechanism for the arm 12. Then, the control unit 28 perform control to prohibit unlocking according to the attachment and detachment state of the image receiving unit 20 on two locking mechanisms, that is, the first locking mechanism 64 and the second locking mechanism 76. As described above, it is preferable to perform control to prohibit unlocking on the two locking mechanisms. However, the control may not be necessarily performed on the two locking mechanisms or may be performed on at least one of the first locking mechanism 64 or the second locking mechanism 76.

Further, in the radiography apparatus 10 according to this embodiment, the control to prohibit unlocking is performed in a state in which it is detected that the image receiving unit 20 is detached from the arm 12. However, in addition to this configuration, the following configuration may be used. That is, in a case in which the restriction of the attachment and detachment of the image receiving unit 20 by the solenoid 56 (an example of the attachment and detachment restriction mechanism) is turned off (detachment is possible) in a state in which the image receiving unit 20 is attached to the arm 12, the control to prohibit the unlocking of the rotation may be performed even though the operation of releasing the lock of the rotation of the arm 12 is performed. According to this configuration, it is possible to prevent the inadvertent detachment of the image receiving unit 20 from the arm 12 by the rotation of the arm 12.

In this case, the control unit 28 determines whether or not the image receiving unit 20 is attached on the basis of the detection signal from the photo sensor 60 which is an example of the first attachment and detachment detection unit and determines whether to turn on or off the restriction of the attachment and detachment of the image receiving unit 20 on the basis of the energized state of the solenoid 56.

Second Embodiment

Next, a radiography apparatus according to a second embodiment of the present disclosure will be described with reference to FIGS. 11 to 17. In addition, the same configurations as those in the first embodiment are denoted by the same reference numerals, and the description thereof will not be repeated. The description is focused on the differences between the first and second embodiments.

Figure 11A:
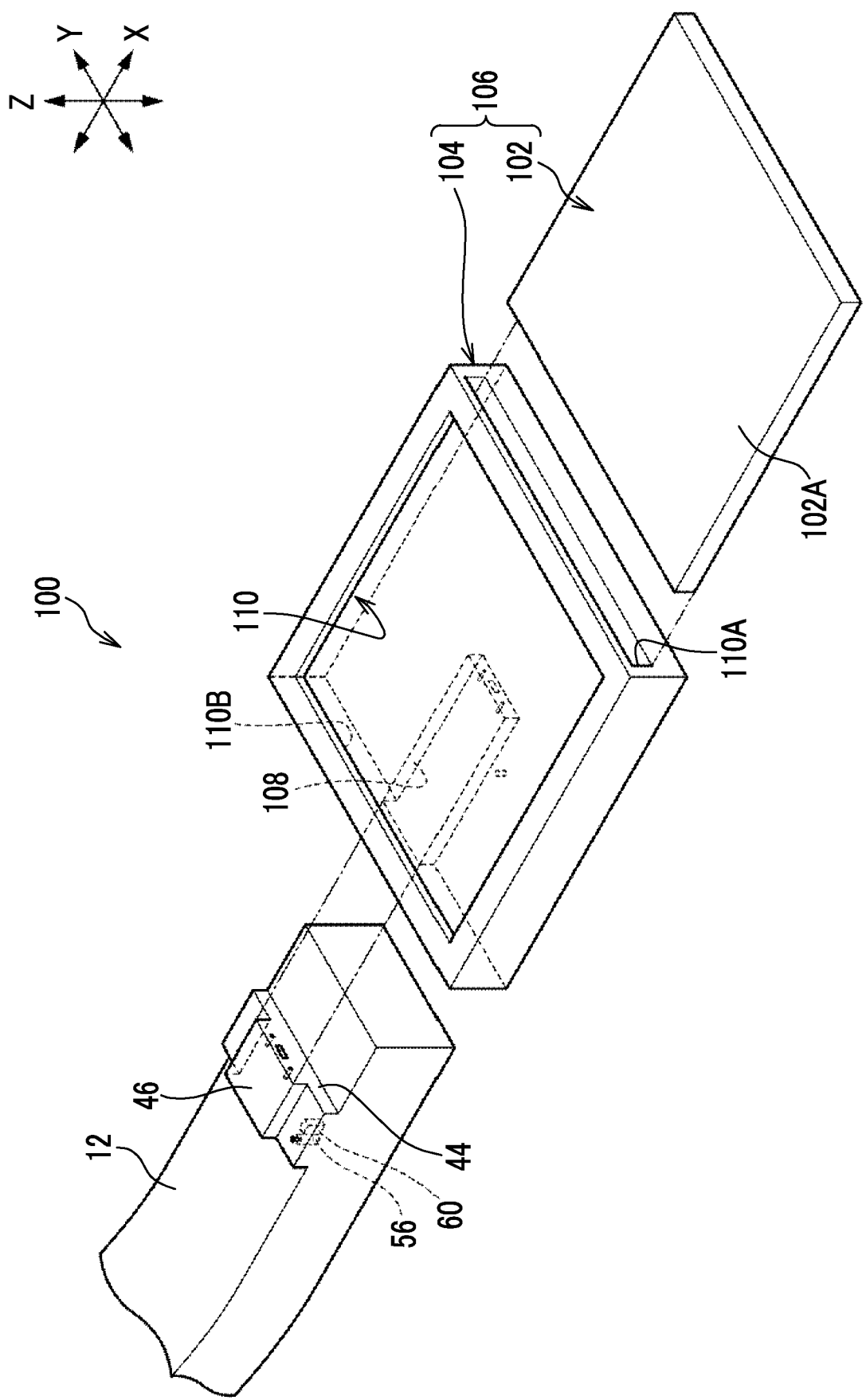
FIG. 11A is a partial perspective view illustrating an image receiving unit of a radiography apparatus according to a second embodiment.
Figure 11B:
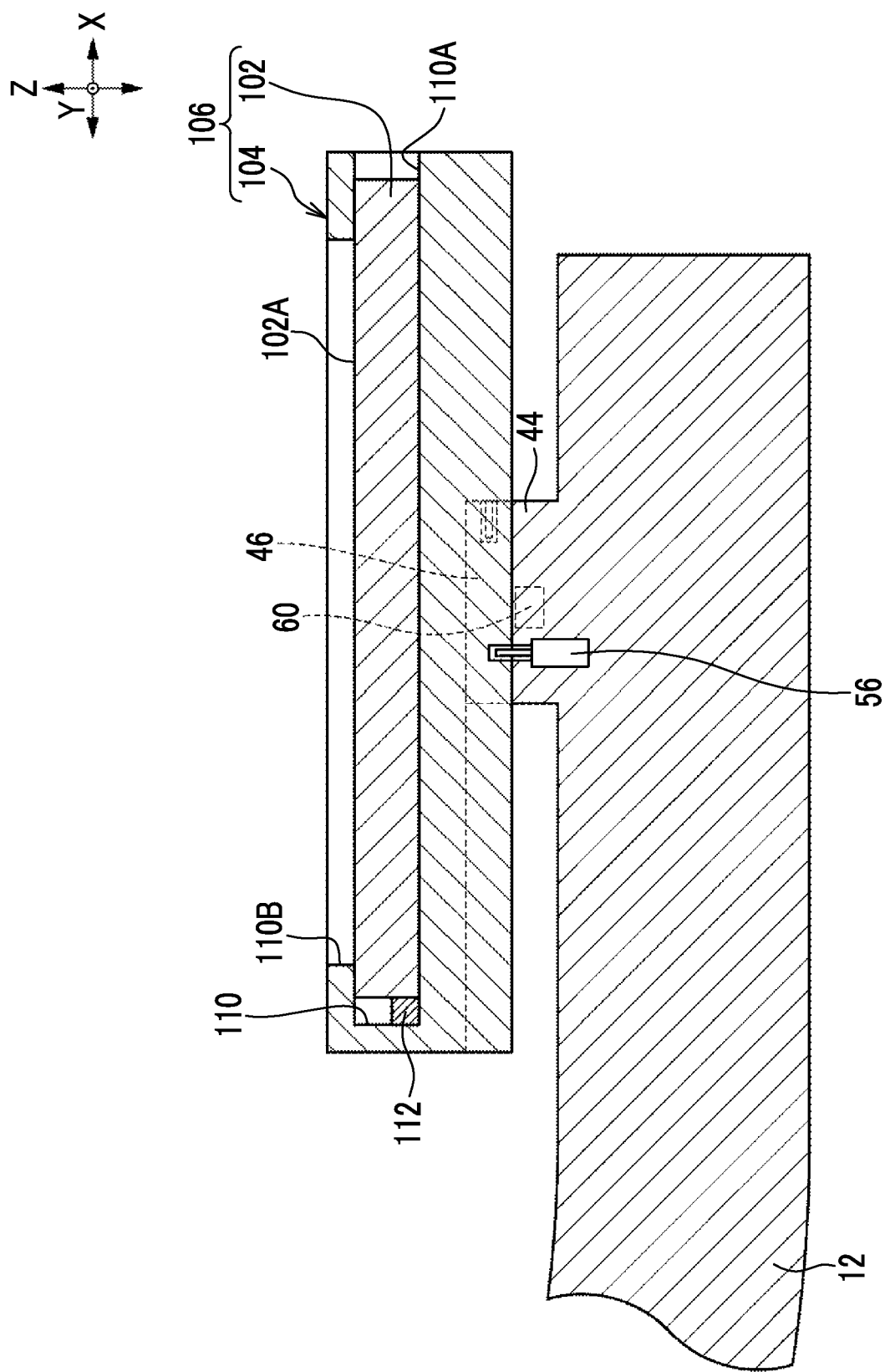
FIG. 11B is a side view illustrating the image receiving unit illustrated in FIG. 11A.

In the radiography apparatus 10 according to the first embodiment, the image receiving unit 20 having the detector that is provided in the housing so as to be undetachable is detachably attached to the arm 12. In contrast, in a radiography apparatus 100 according to this embodiment, as illustrated in FIGS. 11A and 11B, an image receiving unit 106 includes a detector 102 and an accommodation portion 104 in which the detector 102 is accommodated so as to be attachable and detachable.

(Configuration of Image Receiving Unit)

Specifically, the detector 102 is accommodated in the accommodation portion 104 so as to be attachable and detachable, and the accommodation portion 104 is detachably attached to the arm 12. The fact that the detector 102 is attachable to and detachable from the accommodation portion 104 is synonymous with the fact that the detector 102 is attachable to and detachable from the arm 12. Therefore, this configuration makes it possible to change the size of the detector 102 attached to the arm 12.

Further, the accommodation portion 104 can also be attached to and detached from the arm 12. Therefore, in a case in which the size of the detector 102 is changed, it is easy to maintain the weight balance of the arm 12. The weight balance between the irradiation unit 18 and the image receiving unit 106 held at both ends of the C-arm illustrated as an example of the arm 12 is achieved to prevent inadvertent orbital rotation and to keep the arm at any rotational position. Specifically, the center of the orbital rotation of the arm 12 (aligned with the axis line M in FIG. 2A) is aligned with the center of gravity of the entire arm 12 including the irradiation unit 18 and the image receiving unit 106. Therefore, the arm 12 can be kept at any rotational position by the effect of the weight balance of the arm 12.

In a case in which the size of the detector 102 is changed, the weight of the image receiving unit 106 is changed. Therefore, the center of gravity of the arm 12 also deviates from the center of the orbital rotation. Therefore, in addition to the detector 102, the accommodation portion 104 is attachable to and detachable from the arm 12, which makes it possible to compensate a change in the weight of the detector 102 with a change in the weight of the accommodation portion 104. As the accommodation portion 104, for example, a plurality of types of accommodation portions with different weights are prepared by changing, for example, a weight adjusting ballast. The plurality of types of accommodation portions 104 are appropriately used to compensate for a weight change caused by a change in the size of the detector 102. Therefore, even in a case in which the size of the detector 102 is changed, the accommodation portion 104 is changed according to the size change to maintain the weight balance between the irradiation unit 18 and the image receiving unit 106 and to align the center of gravity of the arm 12 with the center of the orbital rotation.

Similarly to the detector according to the first embodiment, the detector 102 constituting the image receiving unit 106 consists of, for example, a flat panel detector and receives the radiation which has been emitted from the irradiation unit 18 illustrated in FIG. 1 and transmitted through the subject H with an image receiving surface 102A to detect a radiographic image of the subject H. In this embodiment, the detector 102 functions as a portable electronic cassette.

The accommodation portion 104 constituting the image receiving unit 106 is a box with a flat rectangular parallelepiped shape and has a fitting recessed portion 108 that is formed in a lower surface and an accommodation recessed portion 110 that accommodates the detector 102. The fitting recessed portion 108 has the same configuration as the fitting recessed portion 48 formed in the lower surface of the image receiving unit 20 according to the first embodiment. The fitting protruding portion 46 provided at the other end of the arm 12 is fitted to the fitting recessed portion 108 such that the accommodation portion 104 is detachably attached to the arm 12.

Further, similarly to the first embodiment, the arm 12 is provided with the solenoid 56 that restricts the attachment and detachment of the accommodation portion 104 to and from the arm 12 and the photo sensor 60 as the first attachment and detachment detection unit. In this embodiment, the photo sensor 60 detects whether or not the accommodation portion 104 is detached from the arm 12, that is, whether or not both the accommodation portion 104 and the detector 102 constituting the image receiving unit 106 are detached from the arm 12.

As illustrated in FIG. 11A, an opening 110A for accommodating the detector 102 in the accommodation recessed portion 110 is formed in one of four side surfaces of the accommodation portion 104. In addition, an opening 110B with a square shape which communicates with the accommodation recessed portion 110 is formed in the upper surface of the accommodation portion 104 which faces the irradiation opening 34A (see FIG. 16) of the irradiation unit 18.

In a state in which the detector 102 is accommodated in the accommodation recessed portion 110, the image receiving surface 102A of the detector 102 is exposed through the opening 110B that is formed in the upper surface of the accommodation portion 104 as illustrated in FIG. 11B. Therefore, even in a state in which the detector 102 is attached to the accommodation portion 104, that is, the arm 12, the radiation emitted from the irradiation unit 18 (see FIG. 16) can be received by the image receiving surface 102A of the detector 102.

Further, the accommodation portion 104 is provided with a photo sensor 112 as a second attachment and detachment detection unit that detects whether or not the detector 102 is detached from the accommodation portion 104. The photo sensor 112 is provided on a side surface of the accommodation portion 104 which is opposite to the side surface in which the opening 110A is formed in the accommodation recessed portion 110.

The photo sensor 112 has the same configuration as the photo sensor 60 according to the first embodiment and detects a change in the amount of light which has been emitted from a light emitting element and then received by a light receiving element to detect whether or not the detector 102 is present in the accommodation recessed portion 110. In addition, the second attachment and detachment detection unit is not limited to the photo sensor 112 and may be, for example, a contact sensor using a piezoelectric element or a microswitch as long as it has a function that can detect whether or not the detector 102 is detached from the accommodation portion 104.

Further, in addition to the photo sensor 112 as the second attachment and detachment detection unit, an attachment and detachment restriction mechanism (not illustrated) that fixes the detector 102 in the accommodation recessed portion 110 to prevent the detector 102 from falling off and releases the fixation may be provided in the accommodation recessed portion 110.

(Configuration of First Friction Mechanism)

Figure 12:
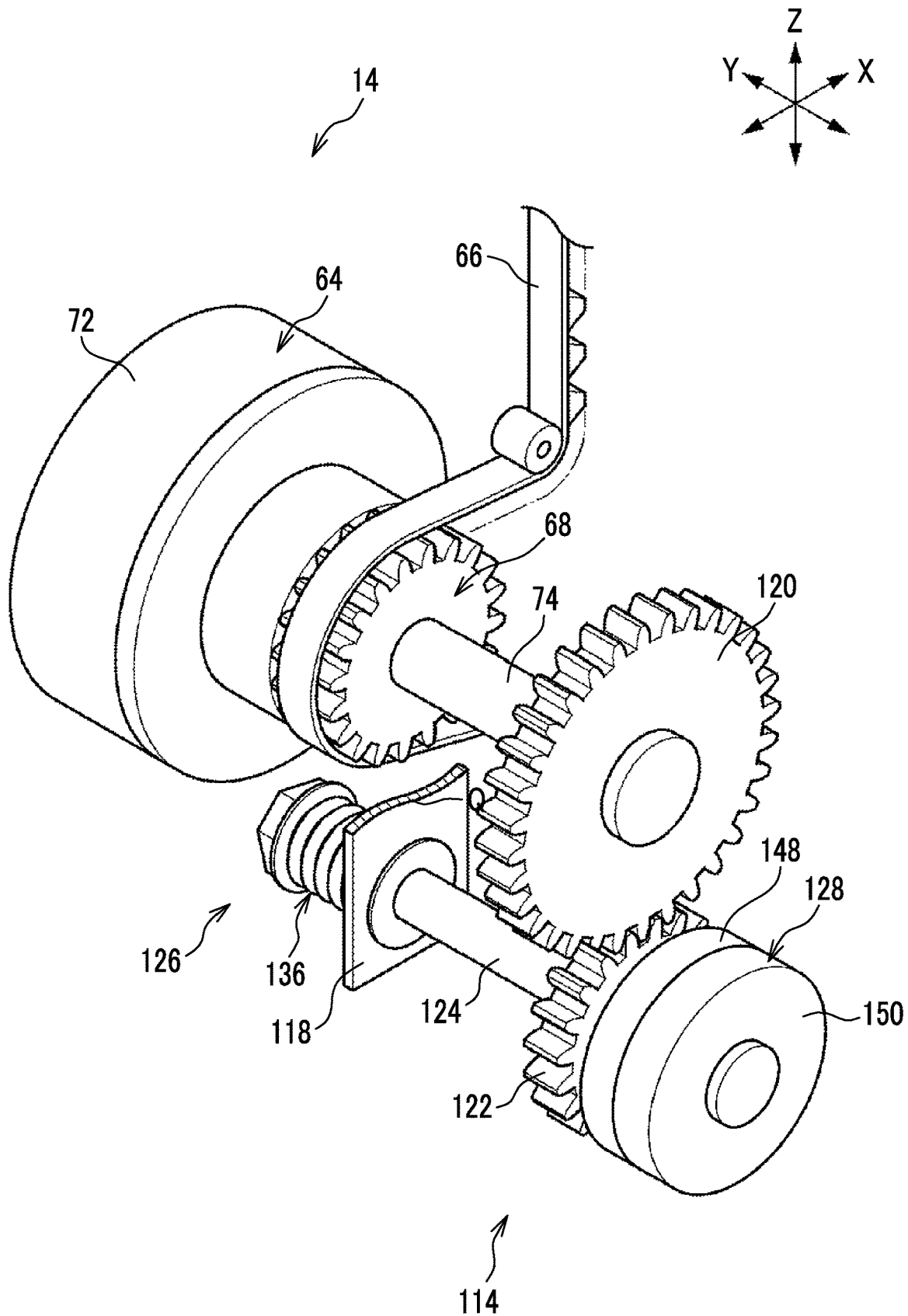
FIG. 12 is a perspective view illustrating a first locking mechanism and a first friction mechanism of the radiography apparatus according to the second embodiment.
Figure 13:
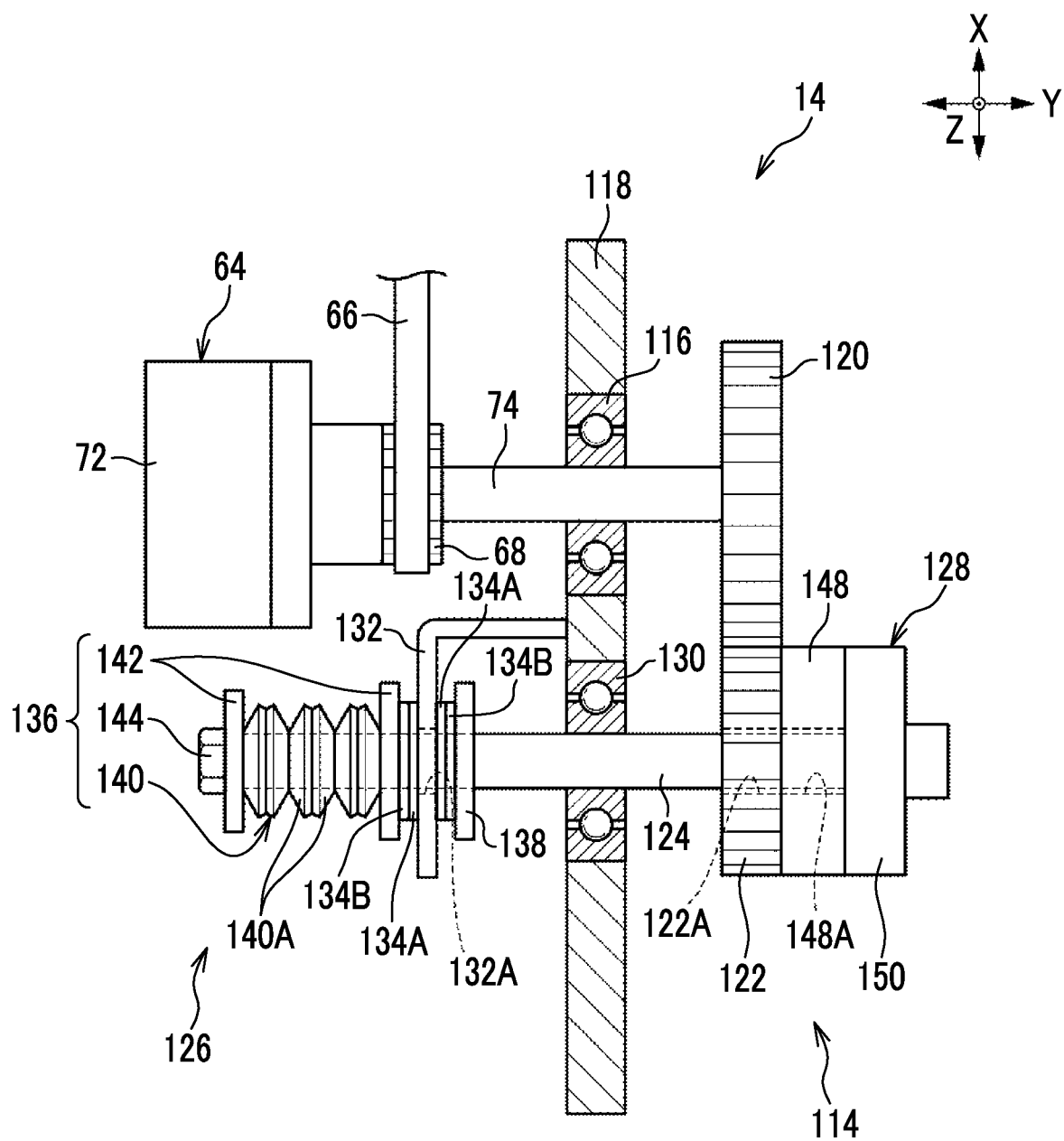
FIG. 13 is a plan view of the first locking mechanism and the first friction mechanism illustrated in FIG. 12.

As illustrated in FIGS. 12 and 13, a connection portion 14 of the radiography apparatus 100 according to this embodiment is provided with a first locking mechanism 64 and a first friction mechanism 114 as a friction mechanism.

The first locking mechanism 64 has the same configuration as that according to the first embodiment. That is, the first locking mechanism 64 has a housing 72 and a rotation shaft 74, and a timing pulley 68 is fixed to the rotation shaft 74. In addition, a timing belt 66 whose both ends are fixed to both ends of the arm 12 is wound around the timing pulley 68.

Further, the rotation shaft 74 of the first locking mechanism 64 is supported by a frame 118 of the connection portion 14 through a bearing portion 116 illustrated in FIG. 13 so as to be rotatable. Furthermore, a first gear 120 is fixed to the rotation shaft 74 so as to be coaxially rotatable, and a second gear 122 is engaged with the first gear 120.

The first friction mechanism 114 includes a first friction shaft 124, a frictional force generation unit 126 that is attached to the first friction shaft 124 and generates a frictional force, and a first electromagnetic clutch 128 that switches connection and disconnection between the rotation shaft 74 of the first locking mechanism 64 and the first friction shaft 124.

As illustrated in FIG. 13, the first friction shaft 124 is supported by the frame 118 of the connection portion 14 through a bearing portion 130 so as to be rotatable. In addition, the first friction shaft 124 is inserted into a shaft hole 132A that is formed in a side plate 132. The side plate 132 is fixed to the frame 118 at a distance from the frame 118 in the axial direction of the first friction shaft 124 (the Y direction in FIG. 13).

The frictional force generation unit 126 comprises two sets of friction plates 134A and 134B that generate a frictional force using contact between friction surfaces and a biasing portion 136 that biases the friction plates 134A and 134B in a direction in which the friction surfaces are pressed. The two sets of friction plates 134A and 134B are provided on both end surfaces of the side plate 132 in the axial direction of the first friction shaft 124, respectively.

A shaft hole (not illustrated) is formed in each of the friction plates 134A and 134B. The first friction shaft 124 is inserted into the shaft holes such that the friction plates 134A and 134B are attached so as to be movable in the axial direction of the first friction shaft 124. In addition, the movement of one set of friction plates 134A and 134B, which is disposed between the side plate 132 and the frame 118, in the axial direction of the first friction shaft 124 is restricted by a restriction plate 138 that is fixed to the first friction shaft 124.

Further, the friction plate 134A that comes into contact with the end surface of the side plate 132 is a fixed friction plate that is fixed by a rotation stopper (not illustrated) and is not rotated regardless of the rotation of the first friction shaft 124. On the other hand, the friction plate 134B that is provided outside the friction plate 134A (fixed friction plate) in the axial direction of the first friction shaft 124 with respect to the side plate 132 is a rotary friction plate that is rotated as the first friction shaft 124 is rotated.

The biasing portion 136 is provided between one end of the first friction shaft 124 in the axial direction and the side plate 132 and comprises a disc spring unit 140, a pair of buffer plates 142, and a nut 144 that is provided at one end of the first friction shaft 124 in the axial direction.

The disc spring unit 140 includes a plurality of disc springs 140A. The disc spring 140A is a disk-shaped spring that has one convex surface and the other concave surface. The plurality of disc springs 140A are arranged along the axial direction of the first friction shaft 124 so as to be stacked.

Further, each of the buffer plates 142 is disposed outside the disc spring unit 140 in the axial direction of the first friction shaft 124. One buffer plate 142 is disposed between the disc spring unit 140 and the friction plate 134B. In addition, the other buffer plate 142 is disposed between the disc spring unit 140 and the nut 144.

Furthermore, a shaft hole (not illustrated) is formed in each of the buffer plate 142 and the disc spring 140A. The first friction shaft 124 is inserted into the shaft holes such that the buffer plate 142 and the disc spring 140A are attached so as to be movable in the axial direction of the first friction shaft 124.

In a case in which the nut 144 is tightened with the end surface of the disc spring unit 140 in contact with one buffer plate 142, the disc spring unit 140 is moved in the direction in which the one buffer plate 142 is pressed. In a case in which the disc spring unit 140 is moved, a pressing force is applied to each set of the friction plates 134A and 134B through the buffer plate 142.

In a case in which the nut 144 is further tightened and the disc spring unit 140 reaches a movement limit, the disc spring 140A is elastically deformed and the disc spring unit 140 contracts in the axial direction of the first friction shaft 124. The disc spring unit 140 biases the friction surfaces of the friction plates 134A and 134B in a direction in which they are pressed against each other on the basis of elasticity.

As described above, the operation of the biasing portion 136 causes the friction surfaces of the friction plates 134A and 134B to come into contact with each other and causes a normal force to be generated on the friction surfaces. Therefore, in a case in which the first friction shaft 124 is rotated, a frictional force acts on the friction surfaces of the friction plates 134A and 134B in a direction opposite to a rotation direction of the first friction shaft 124.

The first electromagnetic clutch 128 is attached to the other end of the first friction shaft 124 in the axial direction. The first electromagnetic clutch 128 comprises a housing 148 having an electromagnet (not illustrated) provided therein and a shaft fixing portion 150 that is fixed to the first friction shaft 124. The housing 148 and the shaft fixing portion 150 are separated from each other. Further, a biasing member (not illustrated) that biases the housing 148 and the shaft fixing portion 150 in a direction in which they become further away from each other is provided between the housing 148 and the shaft fixing portion 150.

The housing 148 of the first electromagnetic clutch 128 is fixed to a second gear 122. Shaft holes 122A and 148A through which the first friction shaft 124 is inserted are formed in the housing 148 and the second gear 122, respectively. Further, a gap is formed between the outer peripheral surface of the first friction shaft 124 and the inner peripheral surfaces of the shaft holes 122A and 148A. That is, the housing 148 and the second gear 122 are not connected to the first friction shaft 124.

The first electromagnetic clutch 128 switches connection and disconnection between the second gear 122 and the first friction shaft 124 to switch connection and disconnection between the rotation shaft 74 of the first locking mechanism 64 and the first friction shaft 124. Specifically, in a case in which the first electromagnetic clutch 128 is energized, a magnetic force is generated in the electromagnet provided in the housing 148, and the shaft fixing portion 150 is attracted to the electromagnet against the biasing force of the biasing member (not illustrated). Therefore, the housing 148 and the shaft fixing portion 150 are closely connected.

In a case in which the rotation shaft 74 is rotated in a state in which the housing 148 is connected to the shaft fixing portion 150 (corresponding to a first state), the first gear 120, the second gear 122, and the housing 148 of the first electromagnetic clutch 128 are rotated with the rotation of the rotation shaft 74. In addition, the shaft fixing portion 150 of the first electromagnetic clutch 128 connected to the housing 148 and the first friction shaft 124 to which the shaft fixing portion 150 is fixed are also rotated with the rotation of the rotation shaft 74.

As described above, a frictional force acts on the first friction shaft 124 in the direction opposite to the rotation direction. Therefore, in a case in which the first friction shaft 124 is rotated with the rotation of the rotation shaft 74, a frictional force acts on the rotation shaft 74 in the direction opposite to the rotation direction.

The timing pulley 68 is fixed to the rotation shaft 74, and the timing belt 66 fixed to both ends of the arm 12 is wound around the timing pulley 68. Therefore, a frictional force acts on the rotation shaft 74 in the direction opposite to the rotation direction. In a case in which the arm 12 is orbitally rotated, a frictional force acts on the arm 12 in a direction opposite to the rotation direction of the arm 12.

On the other hand, in a case in which the first electromagnetic clutch 128 is de-energized, the housing 148 fixed to the second gear 122 and the shaft fixing portion 150 fixed to the first friction shaft 124 are biased by a biasing member (not illustrated) to be separated from each other. Therefore, the housing 148 and the shaft fixing portion 150 are disconnected, and the second gear 122 and the first friction shaft 124 are disconnected.

In a case in which the rotation shaft 74 is rotated in a state in which the housing 148 and the shaft fixing portion 150 are disconnected (corresponding to a second state), the first gear 120, the second gear 122, and the housing 148 of the first electromagnetic clutch 128 are rotated with the rotation of the rotation shaft 74. However, the shaft fixing portion 150 of the first electromagnetic clutch 128 and the first friction shaft 124 are not rotated. Therefore, the frictional force that acts on the first friction shaft 124 in a case in which the rotation shaft 74 is rotated does not act. The frictional force that acts on the arm 12 in a case in which the arm 12 is orbitally rotated is less than that in a case in which the first electromagnetic clutch 128 is energized.

(Configuration of Second Friction Mechanism)

Figure 14:
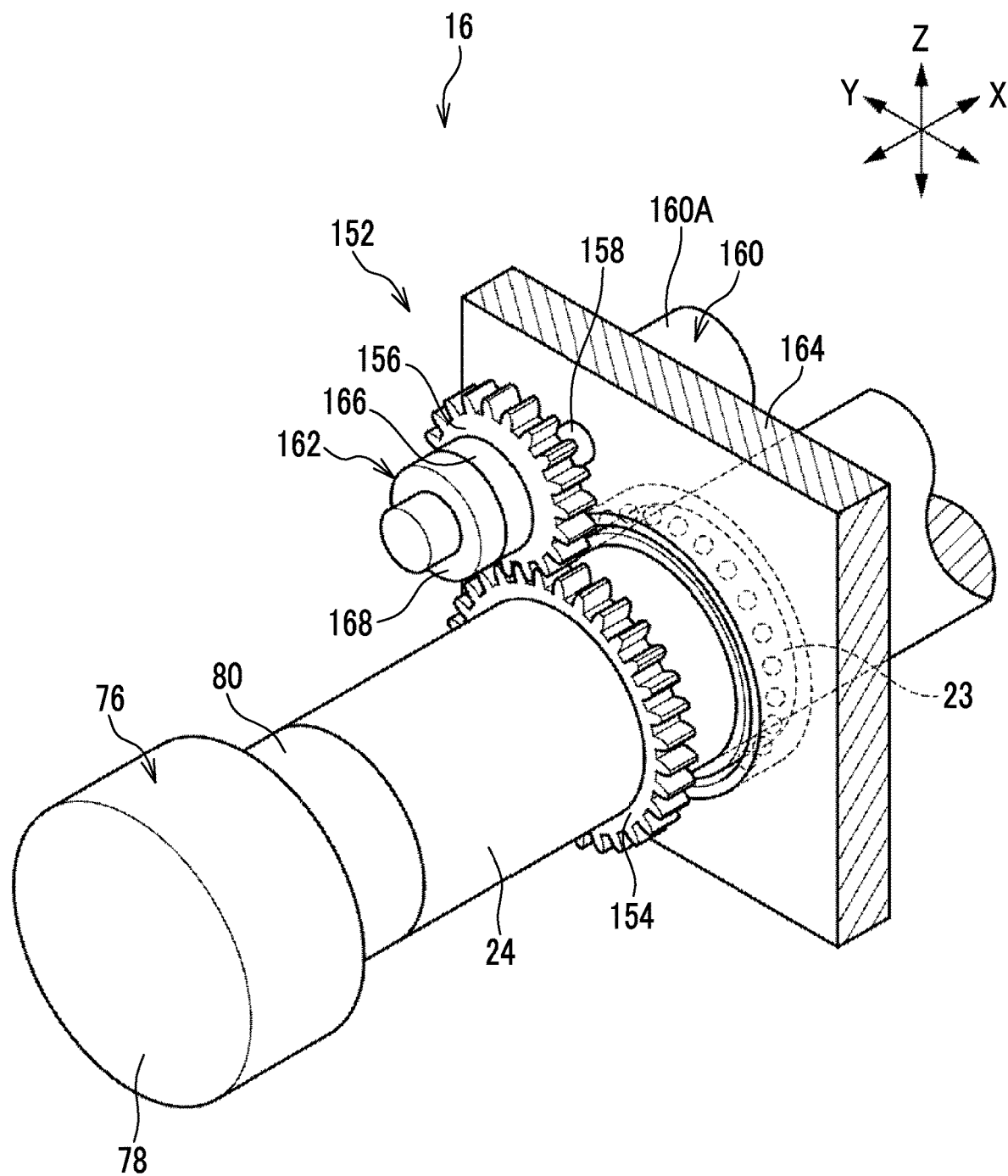
FIG. 14 is a perspective view illustrating a second locking mechanism and a second friction mechanism of the radiography apparatus according to the second embodiment.
Figure 15:
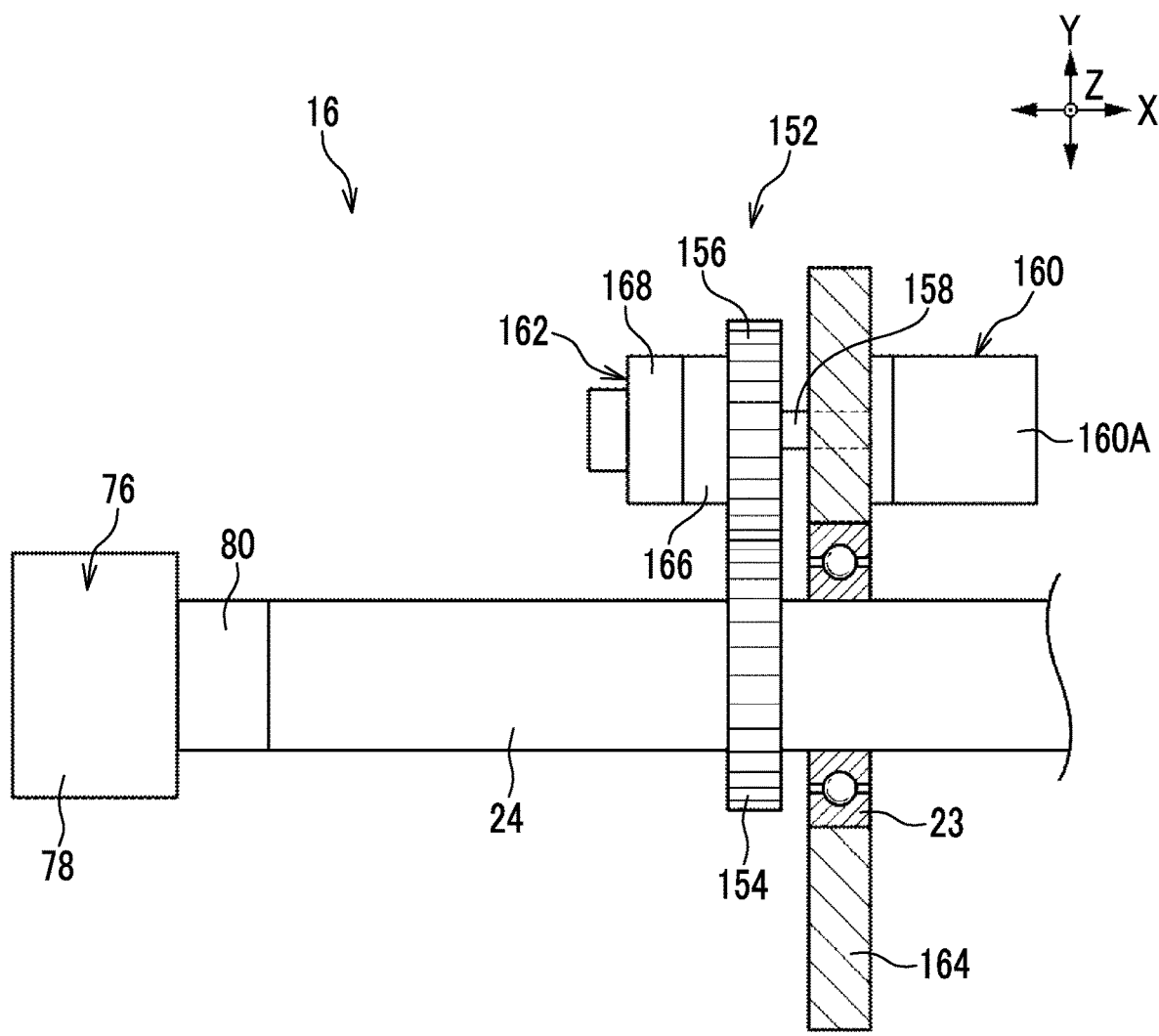
FIG. 15 is a side view illustrating the second locking mechanism and the second friction mechanism illustrated in FIG. 14.

In addition, as illustrated in FIGS. 14 and 15, the main body portion 16 of the radiography apparatus 100 according to this embodiment is provided with a second locking mechanism 76 and a second friction mechanism 152 as a friction mechanism. The second locking mechanism 76 has the same configuration as that in the first embodiment.

That is, the second locking mechanism 76 has a housing 78 and a rotation shaft 80. The other end of the support shaft 24 having one end fixed to the arm 12 (see FIG. 16) is fixed to the rotation shaft 80. In this embodiment, a third gear 154 is fixed to the outer peripheral surface of the support shaft 24 so as to be coaxially rotatable, and a fourth gear 156 is engaged with the third gear 154.

The second friction mechanism 152 includes a second friction shaft 158, a frictional force generation unit 160 that is attached to the second friction shaft 158 and generates a frictional force, and a second electromagnetic clutch 162 that switches connection and disconnection between the support shaft 24 and the second friction shaft 158.

The second friction shaft 158 is supported by a frame 164 of the main body portion 16 through a bearing portion (not illustrated). Further, the frictional force generation unit 160 is attached to one end of the second friction shaft 158 in the axial direction. In this embodiment, the frictional force generation unit 160 is, for example, a rotary damper.

Specifically, the frictional force generation unit 160 comprises a rotor (not illustrated) that is fixed to the one end of the second friction shaft 158 in the axial direction, a housing 160A that accommodates the rotor, and a viscous body (not illustrated) that consists of, for example, oil filled between the rotor and the housing 160A.

In a case in which the second friction shaft 158 is rotated, the rotor fixed to the second friction shaft 158 is rotated in the housing 160A. In this case, a frictional force acts on the outer peripheral surface of the rotor in a direction opposite to the rotation direction by the viscous resistance of the viscous body filled in the housing 160A. That is, the frictional force acts on the second friction shaft 158 in the direction opposite to the rotation direction.

In addition, the second electromagnetic clutch 162 is attached to the other end of the second friction shaft 158 in the axial direction. The second electromagnetic clutch 162 has the same configuration as the first electromagnetic clutch 128 and comprises a housing 166 that is fixed to the fourth gear 156 and a shaft fixing portion 168 that is fixed to the second friction shaft 158.

In a case in which the second electromagnetic clutch 162 is energized, the housing 166 and the shaft fixing portion 168 are connected to each other (corresponding to the first state). The frictional force that acts on the second friction shaft 158 in the direction opposite to the rotation direction acts on the support shaft 24 through the fourth gear 156 and the third gear 154. Then, in a case in which the arm 12 (see FIG. 16) is rotated about the axis, the frictional force acts on the arm 12 in the direction opposite to the rotation direction of the arm 12.

On the other hand, in a case in which the second electromagnetic clutch 162 is de-energized, the housing 166 and the shaft fixing portion 168 are disconnected from each other (corresponding to the second state). The frictional force acting on the second friction shaft 158 does not act on the support shaft 24. Therefore, the frictional force that acts on the arm 12 in a case in which the arm 12 (see FIG. 16) is rotated about the axis is less than that in a case in which the second electromagnetic clutch 162 is energized.

(Configuration of Control Unit)

Figure 16:
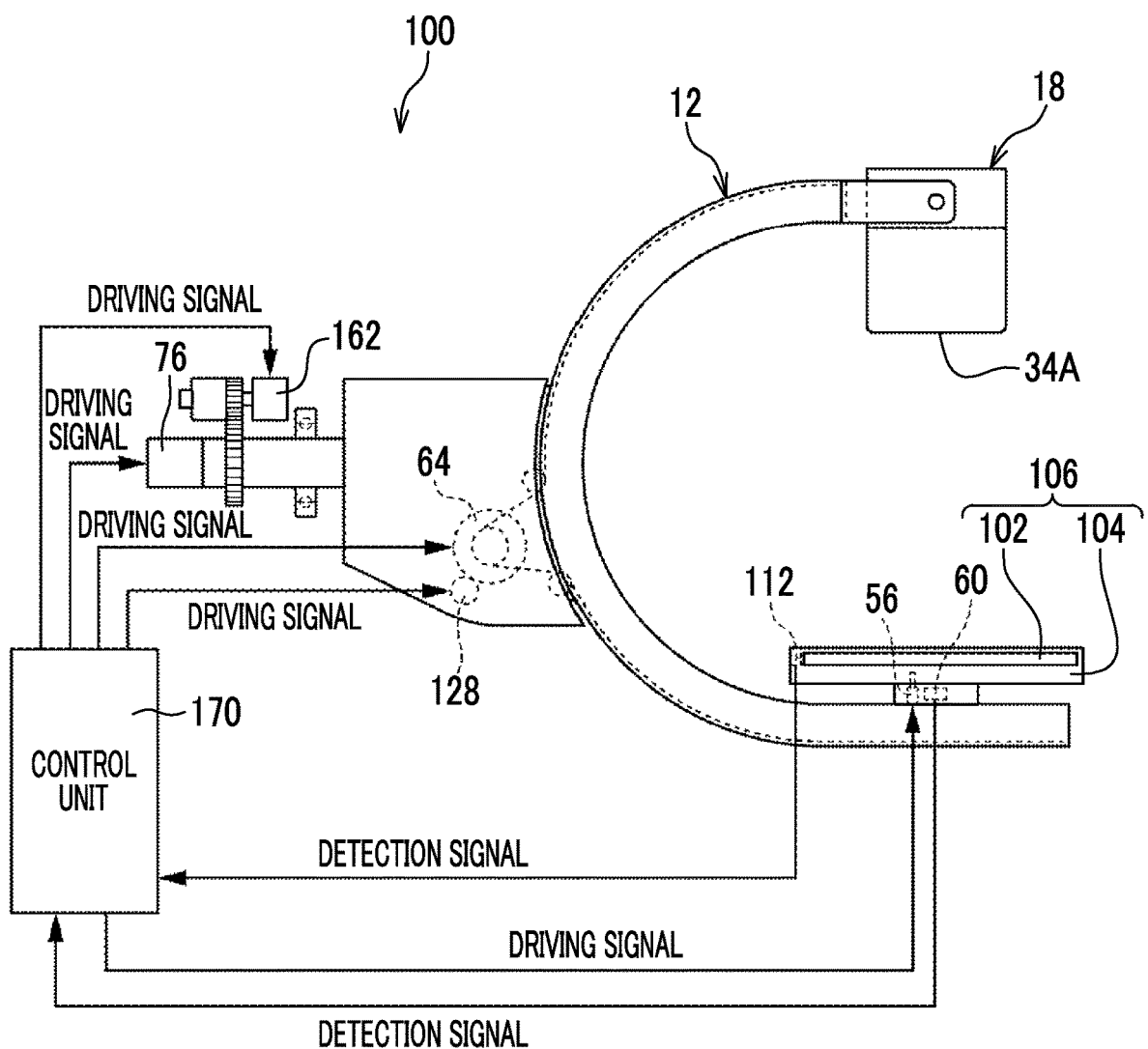
FIG. 16 is a block diagram illustrating a functional configuration of a control unit of the radiography apparatus according to the second embodiment.

As illustrated in FIG. 16, a control unit 170 of the radiography apparatus 100 according to this embodiment controls the energization of the solenoid 56 as in the first embodiment. Therefore, the control unit 170 performs switching between a state in which the attachment and detachment of the accommodation portion 104 to and from the arm 12 are permitted and a state in which the attachment and detachment of the accommodation portion 104 to and from the arm 12 are restricted.

In addition, the control unit 170 determines whether or not the accommodation portion 104 is detached from the arm 12 on the basis of a detection signal from the photo sensor 60 provided in the base 44 of the arm 12 as in the first embodiment. Further, in this embodiment, the control unit 170 determines whether or not the detector 102 is detached from the accommodation portion 104 on the basis of a detection signal from the photo sensor 112 provided in the accommodation recessed portion 110 (see FIG. 11B) of the accommodation portion 104.

Furthermore, the control unit 170 controls the first locking mechanism 64 to switch the locked state of the orbital rotation of the arm 12 and controls the second locking mechanism 76 to switch the locked state of the axial rotation of the arm 12 as in the first embodiment.

Moreover, the control unit 170 controls the first electromagnetic clutch 128. That is, the control unit 170 transmits a driving signal to the first electromagnetic clutch 128 to energize the first electromagnetic clutch 128. Then, the rotation shaft 74 and the first friction shaft 124 illustrated in FIG. 13 are connected, and a frictional force acts on the arm 12 in the direction opposite to the direction of rotation direction.

On the other hand, the control unit 170 de-energizes the first electromagnetic clutch 128 to disconnect the rotation shaft 74 from the first friction shaft 124 as illustrated in FIG. 13. Therefore, the frictional force that acts on the arm 12 is less than that in a case in which the first electromagnetic clutch 128 is energized.

Similarly, the control unit 170 controls the second electromagnetic clutch 162. That is, the control unit 170 transmits a driving signal to the second electromagnetic clutch 162 to energize the second electromagnetic clutch 162. Then, the support shaft 24 and the second friction shaft 158 illustrated in FIG. 15 are connected to each other, and a frictional force acts on the arm 12 in the direction opposite to the rotation direction.

On the other hand, the control unit 170 de-energizes the second electromagnetic clutch 162 to disconnect the support shaft 24 from the second friction shaft 158 as illustrated in FIG. 15. Therefore, the frictional force that acts on the arm 12 is less than that in a case in which the second electromagnetic clutch 162 is energized.

(Method for Controlling Radiography Apparatus)

Next, a method for controlling the radiography apparatus 100 according to this embodiment will be described with reference to a flowchart illustrated in FIG. 17.

First, in Step S600, in a case in which the radiography apparatus 100 is turned on by the operation of a power switch (not illustrated) (Y in Step S600), the control unit 170 starts to control the radiography apparatus 100. In a case in which the control by the control unit 170 is started, it is possible to receive the input of the imaging conditions through the operation panel 30. Further, since the first locking mechanism 64 and the second locking mechanism 76 adopt the same non-excited electromagnetic brakes as those in the first embodiment. Therefore, in this example, in a state in which the radiography apparatus 100 is started, the rotation of the arm 12 is locked.

In Step S602, the control unit 170 determines whether or not an unlock operation for releasing the lock of the rotation of the arm 12 has been performed. In a case in which there is no unlock instruction in Step S602 (N in Step S602), the process proceeds to Step S604, and the rotation-locked state of the arm 12 is maintained. That is, the unlocking of the rotation of the arm 12 is prohibited. Then, the process proceeds to Step S620.

In a case in which there is an unlock instruction in Step S602 (Y in Step S602), the control unit 170 determines whether or not the accommodation portion 104 is attached to the arm 12 (Step S606).

In a case in which the control unit 170 determines in Step S606 that the accommodation portion 104 is not attached to the arm 12 (N in Step S606), the process proceeds to Step S604, and the rotation-locked state of the arm 12 is maintained. That is, the unlocking of the rotation of the arm 12 is prohibited. Then, the process proceeds to Step S620.

In a case in which the control unit 170 determines in Step S606 that the accommodation portion 104 is attached to the arm 12 (Y in Step S606), the control unit 170 determines whether or not the detector 102 is attached to the accommodation portion 104 (Step S608).

In a case in which the control unit 170 determines in Step S608 that the detector 102 is not attached to the accommodation portion 104 (N in Step S608), the control unit 170 switches the first friction mechanism 114 and the second friction mechanism 152 to the first state (Step S610). That is, the control unit 170 energizes the first electromagnetic clutch 128 and the second electromagnetic clutch 162 to connect the housings 148 and 166 and the shaft fixing portions 150 and 168. Then, the control unit 170 energizes the first locking mechanism 64 and the second locking mechanism 76 to unlock the rotation of the arm 12 (Step S614).

In a case in which the control unit 170 determines in Step S608 that the detector 102 is attached to the accommodation portion 104 (Y in Step S608), the control unit 170 switches the first friction mechanism 114 and the second friction mechanism 152 to the second state (Step S612). That is, the control unit 170 de-energizes the first electromagnetic clutch 128 and the second electromagnetic clutch 162 to disconnect the housings 148 and 166 from the shaft fixing portions 150 and 168. Then, the control unit 170 energizes the first locking mechanism 64 and the second locking mechanism 76 to unlock the rotation of the arm 12 (Step S614).

In Step S614, after releasing the lock of the rotation of the arm 12, the control unit 170 waits until the lock operation for locking the rotation of the arm 12 is performed (Step S616). Then, in a case in which there is a lock instruction (Y in Step S616), the control unit 170 de-energizes the first locking mechanism 64 and the second locking mechanism 76 to lock the rotation of the arm 12 (Step S618).

In Step S620, the control unit 170 determines whether or not the radiography apparatus 100 has been turned off by the operation of the power switch (not illustrated) by the operator. Then, in a case in which the radiography apparatus 100 has not been turned off (N in Step S620), the process returns to Step S602. On the other hand, in a case in which the radiography apparatus 100 has been turned off (Y in Step S620), the control unit 170 ends the control of the radiography apparatus 100.

Figure 17:
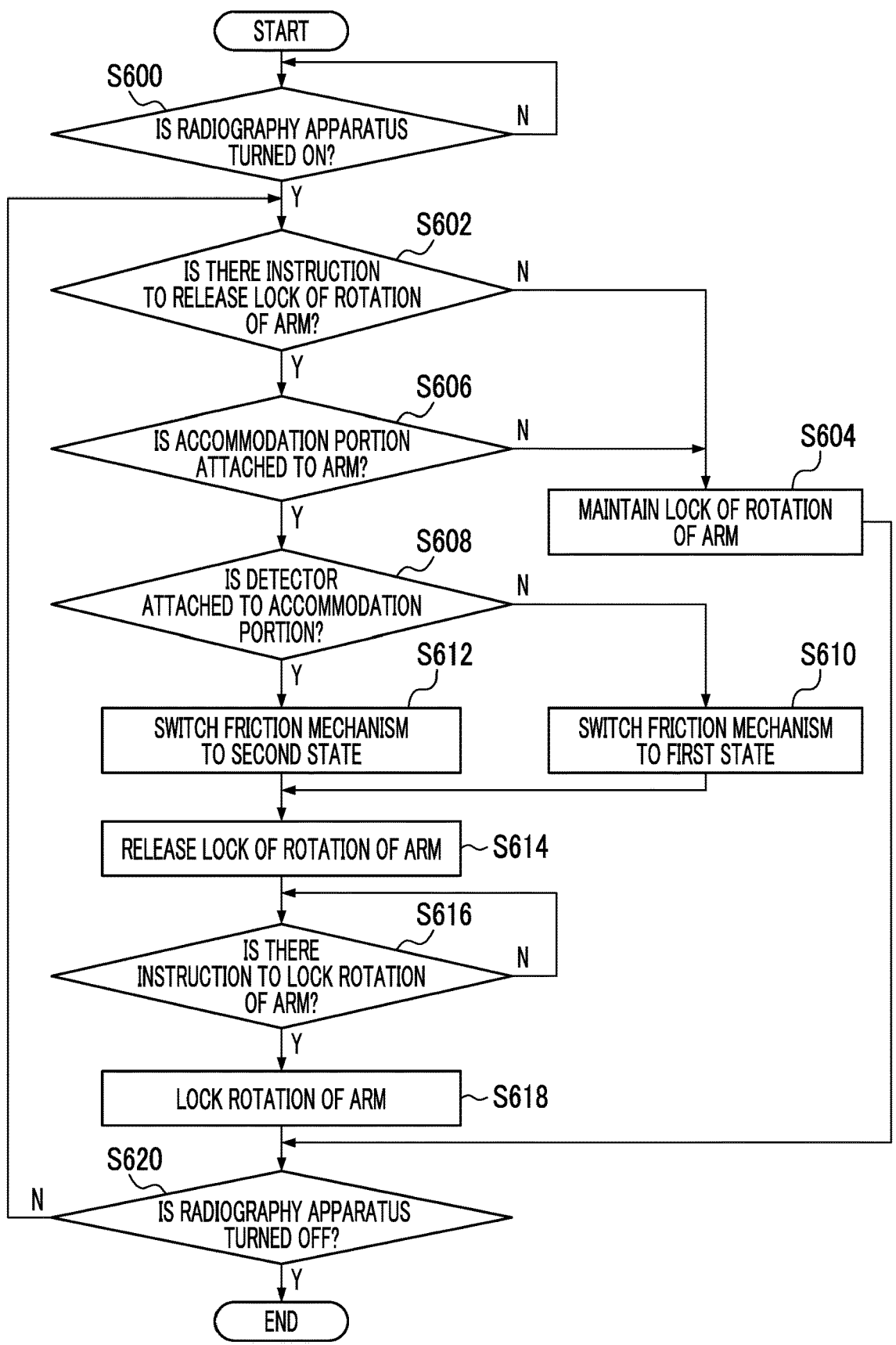
FIG. 17 is a flowchart illustrating a processing procedure of the control unit of the radiography apparatus according to the second embodiment.

Further, in some cases, the radiography apparatus 100 is turned off in a state in which the lock of the rotation of the arm 12 is released in Step S614, which is not illustrated in the flowchart of FIG. 17. In this case, even though the lock instruction is not input through the operation panel 30, the rotation of the arm 12 is locked by turning off the radiography apparatus 100 to de-energize the first locking mechanism 64 and the second locking mechanism 76.

(Operation and Effect)

In the radiography apparatus 100 according to this embodiment, the image receiving unit 106 includes the detector 102 that is accommodated in the accommodation portion 104 so as to be attachable and detachable and the accommodation portion 104 that is held by the arm 12 so as to be attachable and detachable. In addition, the radiography apparatus 100 includes the photo sensor 60 that detects whether or not the accommodation portion 104 is detached from the arm 12 and the photo sensor 112 that detects whether or not the detector 102 is detached from the accommodation portion 104.

Then, in this embodiment, in a state in which the accommodation portion 104 is detached from the arm 12, that is, in a state in which both the accommodation portion 104 and the detector 102 constituting the image receiving unit 106 are detached from the arm 12, the control unit 170 performs control to prohibit the release of the lock of the rotation of the arm 12 even in a case in which the unlock operation is performed. Therefore, it is possible to suppress the inadvertent rotation of the arm 12 in a case in which the accommodation portion 104 of the image receiving unit 106 is detached, without using a complicated mechanism such as a weight balance adjustment mechanism used in the related art.

Further, the radiography apparatus 100 according to this embodiment comprises the first friction mechanism 114 and the second friction mechanism 152. The first friction mechanism 114 and the second friction mechanism 152 have the first electromagnetic clutch 128 and the second electromagnetic clutch 162, respectively. Further, the radiography apparatus 100 can switch between the first state in which a frictional force is applied to the arm 12 and the second state in which the frictional force applied to the arm 12 is less than that in the first state.

In general, in a state in which the accommodation portion 104 is attached to the arm 12 and the detector 102 is detached from the accommodation portion 104, a change in the weight balance of the arm 12 is smaller than that in a state in which both the accommodation portion 104 and the detector 102 are detached from the arm 12.

Here, in this embodiment, it is assumed that the photo sensor 60 which is an example of the first attachment and detachment detection unit detects that the accommodation portion 104 is attached to the arm 12 and the photo sensor 112 which is an example of the second attachment and detachment detection unit detects that the detector 102 is detached from the accommodation portion 104. In this state, in a case in which the unlock operation is performed, the control unit 170 performs control to permit the release of the lock by the first locking mechanism 64 and the second locking mechanism 76 which are an example of the locking mechanism and to switch the first friction mechanism 114 and the second friction mechanism 152 which are an example of the friction mechanism to the first state.

Therefore, it is possible to suppress the inadvertent rotation of the arm 12 with the frictional force while permitting the rotation of the arm 12. In a state in which only the detector 102 is detached from the arm 12, a change in the weight balance of the arm 12 is small. In this case, even in a case in which the rotation of the arm 12 is not completely prohibited by the locking mechanism, it is possible to suppress the inadvertent rotation of the arm 12 with the frictional force. The rotation of the arm 12 is permitted while a load is generated by the frictional force. Therefore, usability is higher than that in a case in which the rotation of the arm 12 is completely prohibited.

On the other hand, in a case in which the unlock operation is performed in a state in which the photo sensor 60 detects that the accommodation portion 104 is attached to the arm 12 and the photo sensor 112 detects that the detector 102 is attached to the accommodation portion 104, the control unit 170 performs control to permit the release of the lock by the first locking mechanism 64 and the second locking mechanism 76 and to switch the first friction mechanism 114 and the second friction mechanism 152 to the second state in which the frictional force is less than the first state. Therefore, the arm 12 can be easily axially or orbitally rotated. Since both the accommodation portion 104 and the detector 102 are attached to the arm 12, the weight balance of the arm 12 is maintained. Even in a case in which the rotation of the arm 12 is permitted, the inadvertent rotation of the arm 12 is suppressed by the action of this weight balance.

In the radiography apparatus 100 according to this embodiment, two locking mechanisms, that is, the first locking mechanism 64 that locks the orbital rotation of the arm 12 and the second locking mechanism 76 that locks the axial rotation of the arm 12, are provided as the locking mechanism for the arm 12. Further, two friction mechanisms, that is, the first friction mechanism 114 corresponding to the orbital rotation of the arm 12 and the second friction mechanism 152 corresponding to the axial rotation of the arm 12, are provided as the friction mechanism. The control unit 170 performs control to prohibit the unlocking of the two locking mechanisms and performs control to switch the two friction mechanisms between the first state and the second state, according to the attachment and detachment state of the accommodation portion 104 and the detector 102 constituting the image receiving unit 106.

As described in this embodiment, it is preferable to perform the control on both the two locking mechanisms and the two friction mechanisms. However, the control may not be necessarily performed on all of them. For example, the control to prohibit the release of the lock may be performed on at least one of the first locking mechanism 64 or the second locking mechanism 76. Further, the control to switch the friction mechanisms between the first state and the second state may be performed on at least one of the first friction mechanism 114 or the second friction mechanism 152.

Third Embodiment

Figure 18:
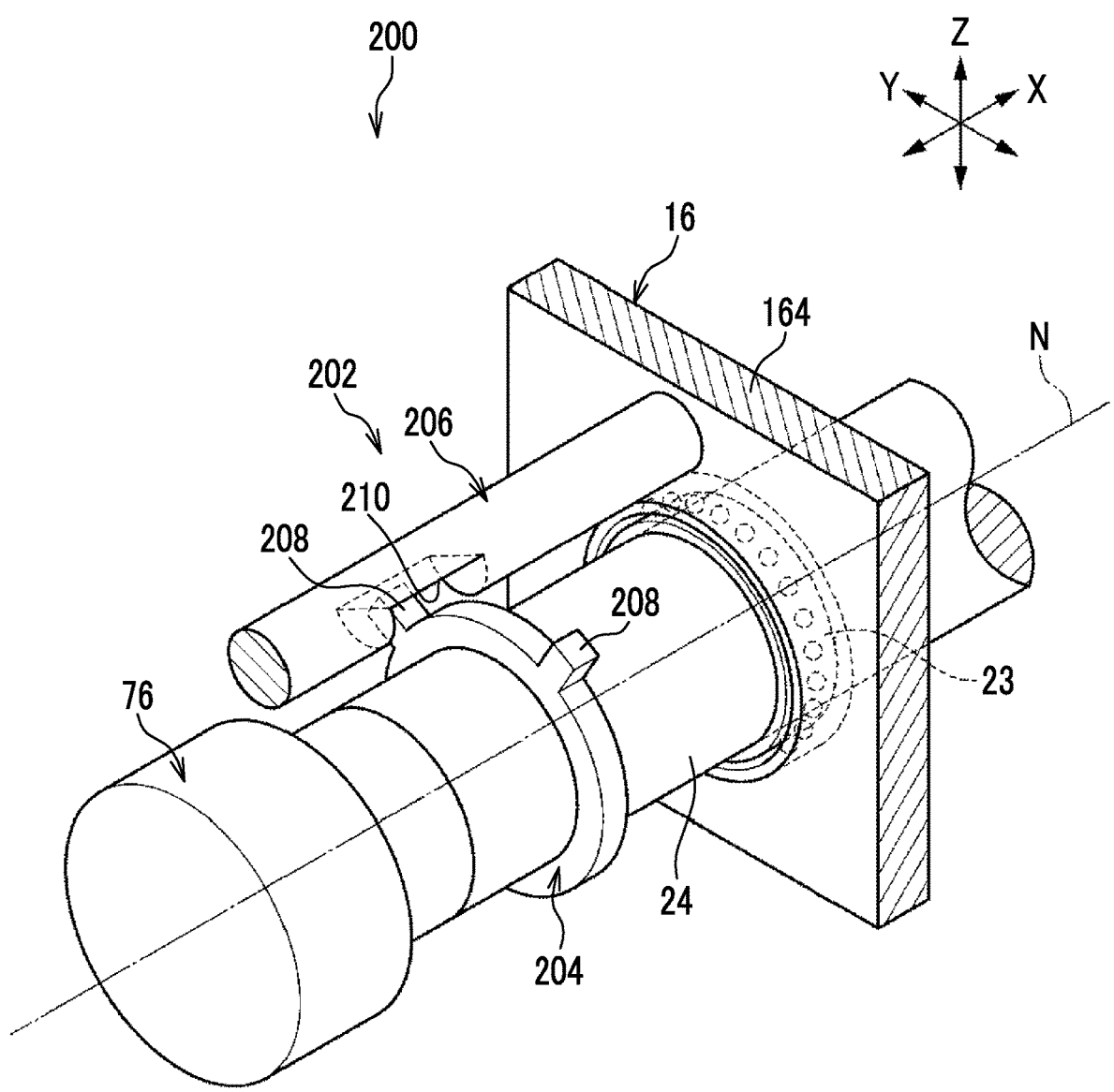
FIG. 18 is a perspective view illustrating a rotation angle restriction mechanism of a radiography apparatus according to a third embodiment.

Next, a radiography apparatus 200 according to a third embodiment of the present disclosure will be described with reference to FIGS. 18 and 19. In addition, the description and illustration of the same configurations as those in the second embodiment will be omitted, and the description is focused on the differences between the second and third embodiments.

In the radiography apparatus 100 according to the second embodiment, the second locking mechanism 76 and the second friction mechanism 152 are provided in the main body portion 16. In contrast, in the radiography apparatus 200 according to this embodiment, a rotation angle restriction mechanism 202 is provided in the main body portion 16 instead of the second friction mechanism 152.

The rotation angle restriction mechanism 202 can switch between a restricted state in which the angular range of the axial rotation of the arm 12 (see FIG. 2A) with respect to the bearing portion 23 is restricted to a second range narrower than a first range and a derestricted state in which the restriction of the rotation angle is released. In addition, in this embodiment, the first range is an angular range of the axial rotation of the arm 12 about the axis line N in a state in which the rotation angle is not restricted by the rotation angle restriction mechanism 202 and is at least equal to or greater than 180°.

Specifically, the rotation angle restriction mechanism 202 comprises a contact member 204 that is fixed to the outer peripheral surface of the support shaft 24 so as to be coaxially rotatable and a cylindrical locking pin 206 that extends in parallel to the support shaft 24, that is, extends in the front-rear direction (X direction) of the radiography apparatus 200.

A pair of protrusions 208 that extend outward in a radial direction of the support shaft 24 are provided on an outer peripheral surface of the contact member 204. The pair of protrusions 208 are disposed at a predetermined interval in a circumferential direction of the support shaft 24. An angle θ (see FIG. 19B) formed between the pair of protrusions 208 and the central axis of the support shaft 24 is within the range (that is, the second range) of the rotation angle of the arm 12 restricted by the rotation angle restriction mechanism 202.

The locking pin 206 is supported by the frame 164 of the main body portion 16 through a bearing portion (not illustrated) so as to be rotatable. In addition, a driving mechanism (not illustrated) that rotates the locking pin 206 is connected to one end of the locking pin 206 in the axial direction.

The locking pin 206 is disposed above the support shaft 24 in the vertical direction (Z direction). In addition, the locking pin 206 is disposed between the pair of protrusions 208 at a position where the support shaft 24 comes into contact with the tip of the protrusion 208 in a case in which the support shaft 24 is rotated about the axis line N. Further, a semicircular cutout 210 is formed at a position that comes into contact with the tip of the protrusion 208 on the outer peripheral surface of the locking pin 206.

Figure 19A:
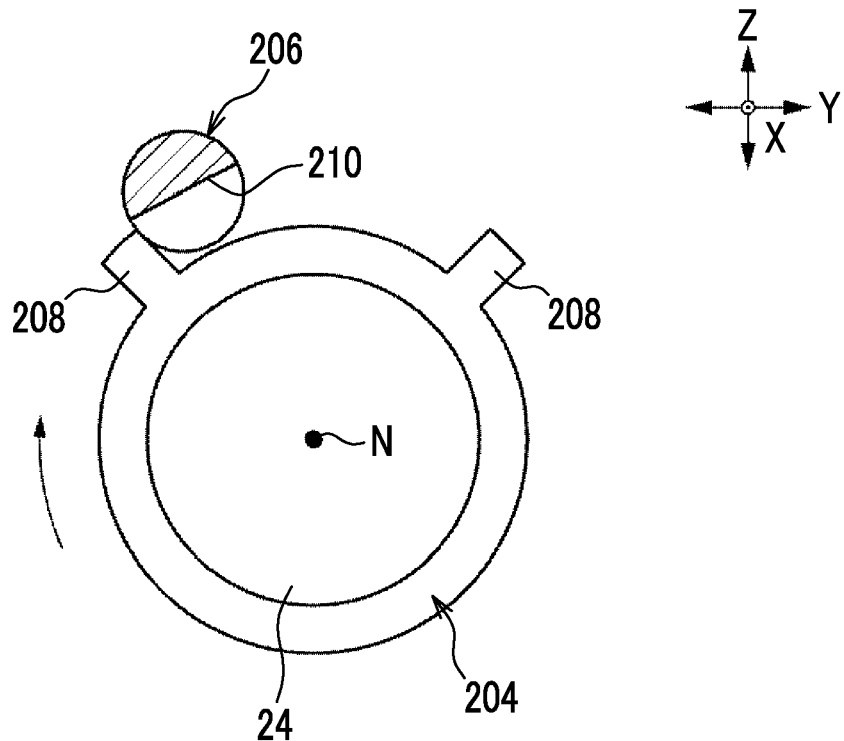
FIG. 19A is a front view illustrating a derestricted state of the rotation angle restriction mechanism illustrated in FIG. 18.
Figure 19B:
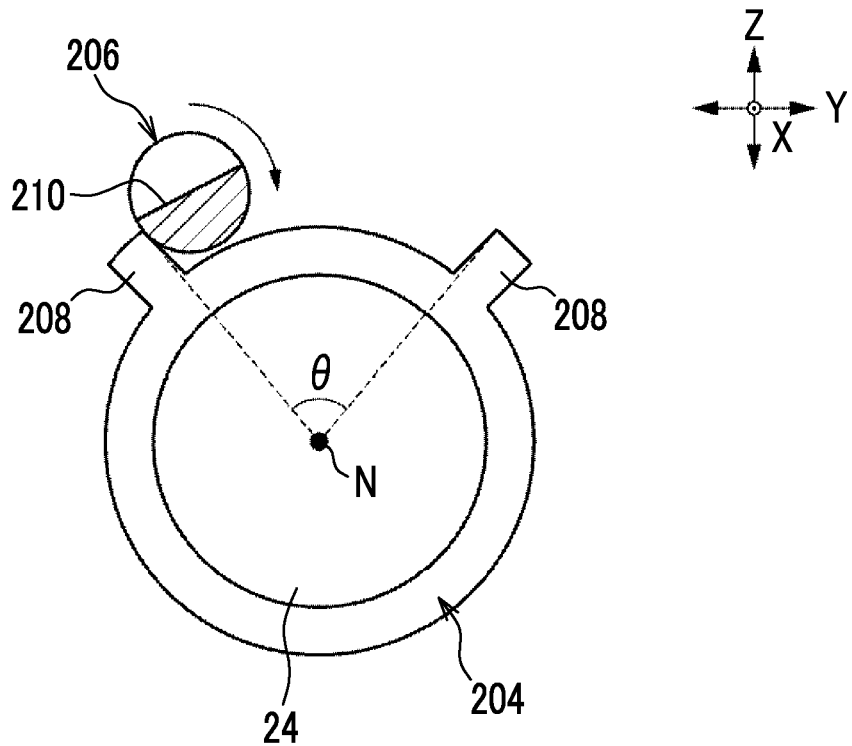
FIG. 19B is a front view illustrating a restricted state of the rotation angle restriction mechanism illustrated in FIG. 18.

As illustrated in FIGS. 19A and 19B, the locking pin 206 can be rotated about the axis by the driving mechanism (not illustrated) to switch between the derestricted state in which the cutout 210 is located on the lower side, that is, on the side facing the protrusion 208 and the restricted state in which the cutout 210 is located on the upper side, that is, on the side opposite to the side facing the protrusion 208.

Specifically, as illustrated in FIG. 19A, in a case in which the locking pin 206 is in the derestricted state and the support shaft 24 is rotated about the axis line N, the protrusions 208 pass through the cutout 210 of the locking pin 206 and do not come into contact with the locking pin 206. Therefore, the rotation of the support shaft 24 is not restricted, and the arm 12 (see FIG. 2A) can be rotated about the axis within the first range.

On the other hand, as illustrated in FIG. 19B, in a case in which the locking pin 206 is at a restriction state and the support shaft 24 is rotated about the axis line N, the protrusions 208 come into contact with the outer peripheral surface of the locking pin 206. Therefore, the support shaft 24 can be rotated only between the angle at which one protrusion 208 comes into contact with the locking pin 206 and the angle at which the other protrusion 208 comes into contact with the locking pin 206. That is, the rotation of the support shaft 24 is restricted by the locking pin 206, and the arm 12 (see FIG. 2A) can be rotated about the axis only within the second range (angle θ).

A control unit according to this embodiment is substantially the same as the control unit 170 according to the second embodiment (see FIG. 16) and is different from the control unit 170 in that, first, it transmits a driving signal to the driving mechanism (not illustrated) to rotate the locking pin 206 such that the locking pin 206 switches between the derestricted state and the restricted state, which is not illustrated.

A control flow procedure of the control unit according to this embodiment is the same as the control flow procedure of the control unit 170 according to the second embodiment. Here, in the control flow according to the second embodiment, in a case in which it is determined in Step S608 that the detector 102 is not attached to the accommodation portion 104 (N in Step S608), the control unit 170 switches the first friction mechanism 114 and the second friction mechanism 152 to the first state (Step S610).

However, in this embodiment, instead of this configuration, in a case in which it is determined in Step S608 that the detector 102 is not attached to the accommodation portion 104 (N in Step S608), the control unit 170 switches the rotation angle restriction mechanism 202 to the restricted state in Step S610.

Further, in the control flow according to the second embodiment, in a case in which it is determined in Step S608 that the detector 102 is attached to the accommodation portion 104 (Y in Step S608), the control unit 170 switches the first friction mechanism 114 and the second friction mechanism 152 to the second state (Step S612).

However, in this embodiment, instead of this configuration, in a case in which the control unit 170 determines in Step S608 that the detector 102 is attached to the accommodation portion 104 (Y in Step S608), the control unit switches the rotation angle restriction mechanism 202 to the derestricted state in Step S612.

(Operation and Effect)

The radiography apparatus 200 according to this embodiment comprises the rotation angle restriction mechanism 202. The rotation angle restriction mechanism 202 is rotated by the driving mechanism (not illustrated). Therefore, the rotation angle restriction mechanism 202 can switch between the restricted state in which the range of the rotation angle of the arm 12 is restricted to the second range narrower than the first range and the derestricted state in which the restriction of the rotation angle is released.

In the second embodiment, as described above, in general, in a state in which the accommodation portion 104 is attached to the arm 12 and the detector 102 is detached from the accommodation portion 104, a change in the weight balance of the arm 12 is smaller than that in a state in which both the accommodation portion 104 and the detector 102 are detached from the arm 12.

Here, in this embodiment, in a case in which the unlock operation is performed in a state in which the photo sensor 60 which is an example of the first attachment and detachment detection unit detects that the accommodation portion 104 is attached to the arm 12 and the photo sensor 112 which is an example of the second attachment and detachment detection unit detects that the detector 102 is detached from the accommodation portion 104, the control unit 170 performs control to permit the release of the lock by the locking mechanism (the first locking mechanism 64 and the second locking mechanism 76) and to switch the rotation angle restriction mechanism 202 to the restricted state. In a state in which only the detector 102 is detached from the arm 12, a change in the weight balance of the arm 12 is small. In this case, the rotation of the arm 12 in a relatively narrow angular range is permitted, which makes it possible to ensure usability while suppressing the inadvertent rotation of the arm 12 in a large angular range.

On the other hand, in a case in which the unlock operation is performed in a state in which the photo sensor 60 detects that the accommodation portion 104 is attached to the arm 12 and the photo sensor 112 detects that the detector 102 is attached to the accommodation portion 104, the control unit 170 performs control to permit the release of the lock by the first locking mechanism 64 and the second locking mechanism 76 and to switch the rotation angle restriction mechanism 202 to the derestricted state.

Therefore, the arm 12 can be axially or orbitally rotated in the state in which the restriction of the rotation angle is released (first range). Since both the accommodation portion 104 and the detector 102 are attached to the arm 12, the weight balance of the arm 12 is maintained. The action of the weight balance makes it possible to suppress the inadvertent rotation of the arm 12 in a large angular range even in a case in which the restriction of the rotation angle of the arm 12 is released.

Other Embodiments

Examples of the embodiments of the present disclosure have been described above. However, the present disclosure is not limited to the above-described embodiments, and various modifications and changes can be made without departing from the gist of the present disclosure. Further, the configurations of each of the above-described embodiments can be appropriately combined with each other.

For example, in the third embodiment, the rotation angle restriction mechanism 202 is provided instead of the second friction mechanism 152 according to the second embodiment. However, the rotation angle restriction mechanism 202 may be provided instead of the first friction mechanism 114 according to the second embodiment. In this case, the angular range of the orbital rotation of the arm 12 can be restricted by the rotation angle restriction mechanism 202.

Furthermore, the rotation angle restriction mechanism 202 according to the third embodiment may be provided in addition to the first friction mechanism 114 or the second friction mechanism 152 according to the second embodiment. In this case, the range of the rotation angle of the arm 12 can be restricted by the rotation angle restriction mechanism 202 while a frictional force is applied to the arm 12 by the first friction mechanism 114 or the second friction mechanism 152 in the direction opposite to the rotation direction.

Moreover, in the first embodiment and the second embodiment, the orbital rotation of the arm 12 is locked by the first locking mechanism 64, and the axial rotation of the arm 12 is locked by the second locking mechanism 76. However, the arm 12 may be configured such that at least one of the orbital rotation or the axial rotation is locked.

In addition, in the second embodiment, two friction mechanisms, that is, the first friction mechanism 114 and the second friction mechanism 152, are provided as the friction mechanism. However, only one of the first friction mechanism 114 and the second friction mechanism 152 may be provided as the friction mechanism.

Further, in the first to third embodiments, it may be determined whether or not the irradiation unit 18 continuously emits radiation, that is, whether or not a moving image is captured, and the release of the lock of the rotation of the arm 12 may be prohibited while the irradiation unit 18 continuously emits the radiation.

Figure 20:
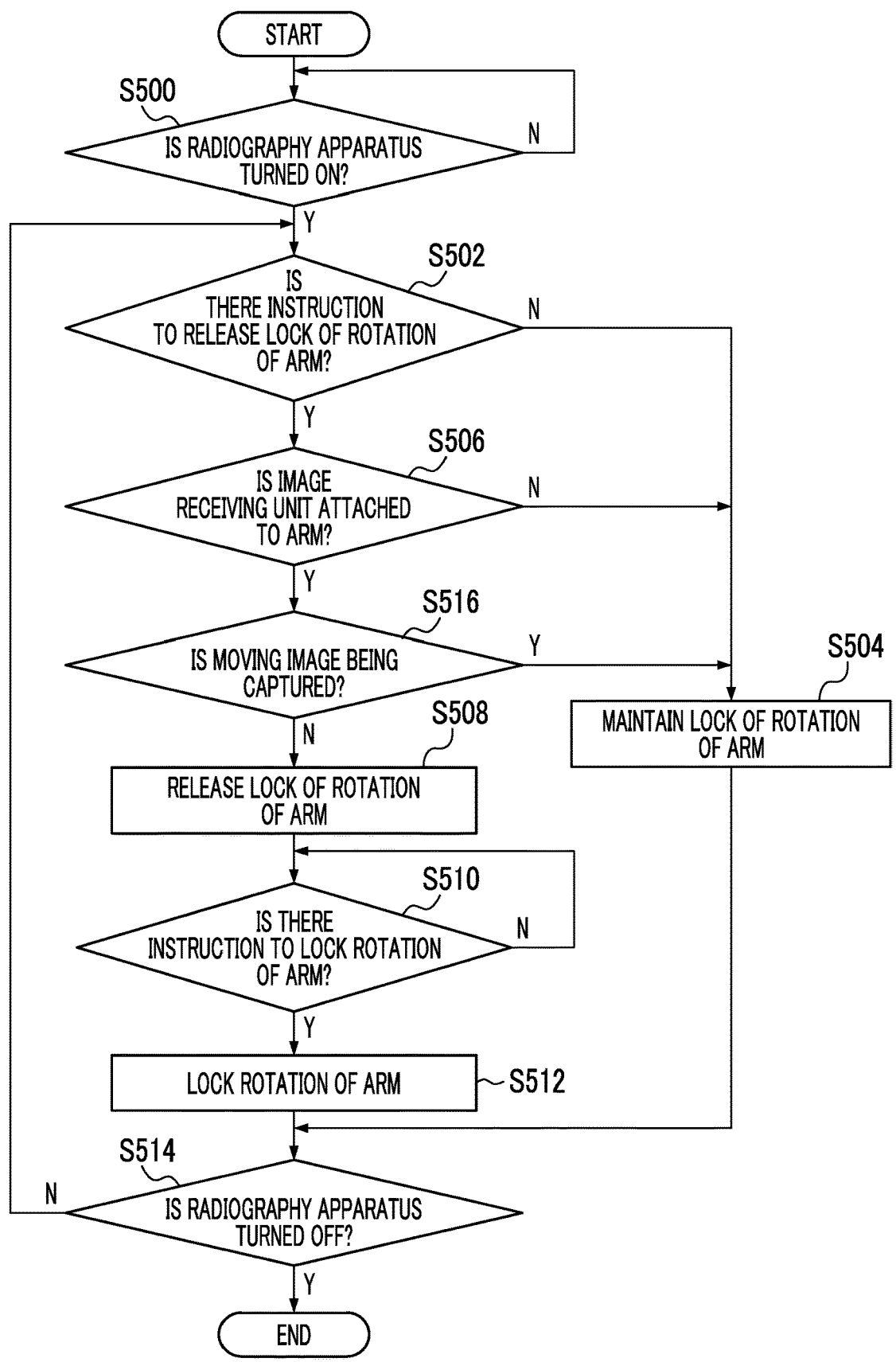
FIG. 20 is a flowchart illustrating a processing procedure of a control unit of a radiography apparatus according to a modification example.

Specifically, as illustrated in FIG. 20, for example, in the control flow according to the first embodiment, Step S516 in which it is determined whether or not a moving image is being captured may be added between Steps S506 and S508. That is, in a case in which it is determined that the image receiving unit 20 (that is, the detector) is attached to the arm 12 (Y in Step S506), the control unit 28 determines whether or not a moving image is being captured (Step S516).

Then, in a case in which a moving image is not being captured (N in Step S516), the lock of the rotation of the arm 12 is released (Step S508). In a case in which a moving image is being captured (Y in Step S516), the rotation-locked state of the arm is maintained (Step S504). That is, the unlocking of the rotation of the arm 12 is prohibited.

According to the above configuration, in a case in which the image receiving unit 20 is attached to the arm 12, the release of the rotation of the lock of the arm 12 is prohibited during the capture of a moving image when the irradiation unit 18 continuously emits radiation even though the unlock operation is performed. Therefore, it is possible to suppress the unnecessary irradiation of parts other than a target imaging part with radiation by the inadvertent rotation of the arm 12.

Further, in the first embodiment, the fitting recessed portion 48 of the image receiving unit 20 (that is, the detector) is fitted to the fitting protruding portion 46 provided at the other end of the arm 12 to attach the image receiving unit 20 to the arm 12 so as to be detachable. However, a method for attaching and detaching the image receiving unit 20 to and from the arm 12 is not limited to the configuration according to the first embodiment.

Figure 21:
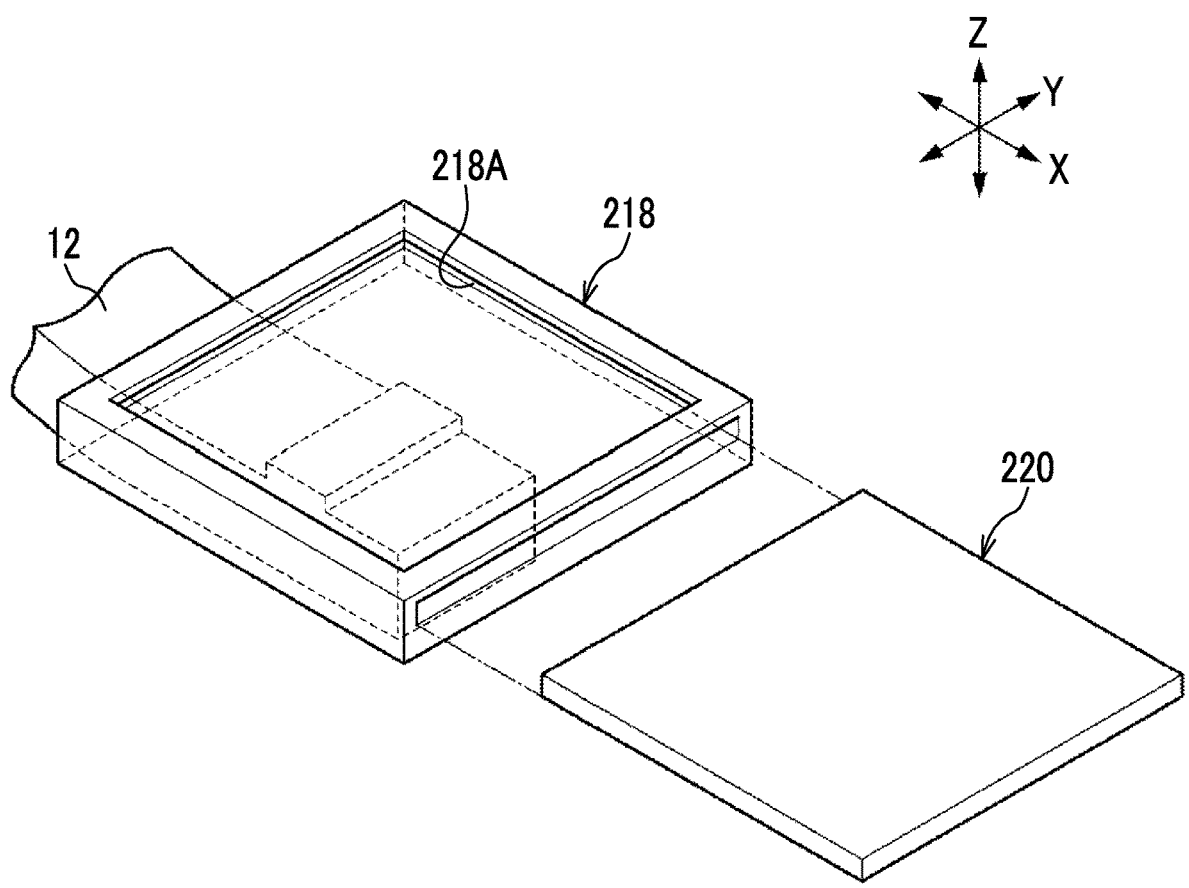
FIG. 21 is a partial perspective view illustrating an image receiving unit of the radiography apparatus according to the modification example.

For example, as illustrated in FIG. 21, a mounting portion 218 in which a mounting recessed portion 218A is formed may be fixed to the other end of the arm 12, and an image receiving unit 220 (that is, a detector) may be accommodated in the mounting recessed portion 218A of the mounting portion 218 so as to be attachable and detachable. In this case, as in the first embodiment, the rotation of the arm 12 is locked in a case in which the image receiving unit 220 is detached from the mounting portion 218. The lock of the rotation of the arm 12 is released in a case in which the image receiving unit 220 is attached to the mounting portion 218.

According to the above-described configuration, the image receiving unit 220 can be accommodated in the mounting recessed portion 218A of the mounting portion 218 to be attached to the arm 12. Therefore, unlike the image receiving unit 20 according to the first embodiment, it is not necessary to form a fitting recessed portion or the like in a lower surface of the image receiving unit 220, and it is easy to use, for example, the ready-made image receiving unit 220.

Further, in the second embodiments, the "second state" of the first friction mechanism 114 and the second friction mechanism 152 is a state in which the frictional force of the first friction shaft 124 and the second friction shaft 158 does not act on the arm 12 (a state in which the acting frictional force is 0). However, the "second state" may be a state in which at least the frictional force acting on the arm 12 is less than that in the "first state" and is not limited to the state in which the frictional force is 0. For example, the first friction mechanism 114 may be switched to the "second state" by adjusting the tightening force of the nut 144 illustrated in FIG. 13 such that the frictional force acting on the first friction shaft 124 is less than that in the "first state".

Further, in the third embodiment, the distance (angle θ) between the pair of protrusions 208 is fixed, and the range of the rotation angle of the arm 12 that can be restricted by the rotation angle restriction mechanism 202 is only the second range. However, the range of the rotation angle of the arm 12 that can be restricted may be variable by changing a protruding position of the protrusion 208 on the outer peripheral surface of the contact member 204. In this case, for example, the rotatable range of the arm 12 can be changed by the weight of the image receiving unit 106 that is attached to and detached from the arm 12 (the magnitude of change in the weight balance).

Further, in each of the above-described embodiments, the arm (C-arm) that can be orbitally rotated and can be rotated about the axis has been described as an example of the arm 12. However, an arm (for example, a U-arm having a U-shape in a side view) that can be only rotated about the axis may be used. Similarly to the C-arm, the U-arm can hold, for example, the irradiation unit 18 and, for example, the image receiving unit 20, 106, or 120 in a posture in which they face each other.

In addition, X-rays have been described as an example of the radiation. However, the present disclosure is not limited to the X-rays. For example, γ-rays may be used.

In each of the above-described embodiments, for example, the following various processors can be used as a hardware structure of processing units performing various processes, such as the control units 28 and 170. The various processors include, for example, a CPU which is a general-purpose processor executing software to function as various processing units as described above, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one integrated circuit (IC) chip is used. A representative example of this aspect is a system on chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

The disclosures of JP2019-199332 filed on Oct. 31, 2019 and JP2019-180016 filed on Sep. 30, 2019 are incorporated herein by reference in their entirety. All of the documents, patent applications, and technical standards described in the specification are incorporated herein by references to the same extent as the incorporation of the individual documents, patent applications, and technical standards by references are described specifically and individually.

What is claimed is:

1. A radiography apparatus comprising:
an irradiation unit that emits radiation;
an arm that holds the irradiation unit and an accommodation portion in which a detector that receives the radiation, which has been emitted from the irradiation unit and transmitted through a subject, to detect a radiographic image of the subject, is attachably and detachably accommodated, in a facing posture such that the accommodation portion is attachable and detachable;
a support portion that rotatably supports the arm;
a locking mechanism that locks a rotation of the arm with respect to the support portion;
a first attachment and detachment detection unit that detects whether or not the accommodation portion is detached from the arm;
a control unit that performs control not to release the lock even in a case in which an unlock operation for releasing the lock of the rotation by the locking mechanism is performed in a state in which the first attachment and detachment detection unit detects that the accommodation portion is detached from the arm;
a friction mechanism that is switchable between a first state in which a frictional force is applied to the arm in a direction opposite to a direction in which the arm is rotated and a second state in which the frictional force applied to the arm is less than the frictional force in the first state; and
a second attachment and detachment detection unit that detects whether or not the detector is detached from the accommodation portion,
wherein the first attachment and detachment detection unit detects whether or not the accommodation portion is detached from the arm, and
in a case in which the unlock operation is performed in a state in which the first attachment and detachment detection unit detects that the accommodation portion is attached to the arm and the second attachment and detachment detection unit detects that the detector is detached from the accommodation portion, the control unit performs control to permit the release of the lock by the locking mechanism and to switch the friction mechanism to the first state.

2. The radiography apparatus according to claim 1, wherein, in a case in which the unlock operation is performed in a state in which the first attachment and detachment detection unit detects that the accommodation portion is attached to the arm and the second attachment and detachment detection unit detects that the detector is attached to the accommodation portion, the control unit performs control to permit the release of the lock by the locking mechanism and to switch the friction mechanism to the second state.

3. The radiography apparatus according to claim 1, wherein the arm has an arc shape in a side view, the support portion includes a track portion that supports the arm to be movable along the arc shape, and the arm is moved with respect to the track portion to be orbitally rotatable about a center of the arc shape as a rotation center.

4. The radiography apparatus according to claim 1, wherein the support portion includes a bearing portion that supports one end of a support shaft having the other end fixed to the arm, and the arm is rotated about the support shaft with respect to the bearing portion to reverse positions of the irradiation unit and the accommodation portion with respect to the subject.

5. The radiography apparatus according to claim 1, wherein, while the irradiation unit continuously emits the radiation in a state in which the first attachment and detachment detection unit detects that the accommodation portion is attached to the arm, the control unit performs control not to release the lock even in a case in which the unlock operation for releasing the lock of the rotation by the locking mechanism is performed.

6. A radiography apparatus comprising:
an irradiation unit that emits radiation;
an arm that holds the irradiation unit and an accommodation portion in which a detector that receives the radiation, which has been emitted from the irradiation unit and transmitted through the subject, to detect a radiographic image of the subject, is attachably and detachably accommodated, in a facing posture such that the accommodation portion is attachable and detachable;
a support portion that rotatably supports the arm;
a locking mechanism that locks a rotation of the arm with respect to the support portion;
a first attachment and detachment detection unit that detects whether or not the accommodation portion is detached from the arm;
a control unit that performs control not to release the lock even in a case in which an unlock operation for releasing the lock of the rotation by the locking mechanism is performed in a state in which the first attachment and detachment detection unit detects that the accommodation portion is detached from the arm;
a rotation angle restriction mechanism that is switchable between a restricted state in which a range of a rotation angle of the arm is restricted to a second range narrower than a first range and a derestricted state in which a restriction of the rotation angle is released; and
a second attachment and detachment detection unit that detects whether or not the detector is detached from the accommodation portion,
wherein the first attachment and detachment detection unit detects whether or not the accommodation portion is detached from the arm, and
in a case in which the unlock operation is performed in a state in which the first attachment and detachment detection unit detects that the accommodation portion is attached to the arm and the second attachment and detachment detection unit detects that the detector is detached from the accommodation portion, the control unit performs control to permit the release of the lock by the locking mechanism and to switch the rotation angle restriction mechanism to the restricted state.

7. The radiography apparatus according to claim 6, wherein, in a case in which the unlock operation is performed in a state in which the first attachment and detachment detection unit detects that the accommodation portion is attached to the arm and the second attachment and detachment detection unit detects that the detector is attached to the accommodation portion, the control unit performs control to permit the release of the lock by the locking mechanism and to switch the rotation angle restriction mechanism to the derestricted state.

* * * * *